US012629067B2

(12) United States Patent     (10) Patent No.:    US 12,629,067 B2

Meehan et al.       (45) Date of Patent:      May 19, 2026

(54) LIGHT EMITTING DIODE TEMPERATURE ESTIMATION

(71) Applicant: Covidien LP, Mansfield, MA (US)

(72) Inventors: Christopher J. Meehan, Denver, CO (US); Jacob D. Dove, Lafayette, CO (US); Julia Taussig, Broomfield, CO (US); Shao-Nung Liang, Broomfield, CO (US); David VandeRiet, Lafayette, CO (US)

(73) Assignee: Covidien LP, Mansfield, MA (US)

( * ) Notice: Subject to any disclaimer, the term of this patent is extended or adjusted under 35 U.S.C. 154(b) by 619 days.

(21) Appl. No.: 18/045,959

(22) Filed: Oct. 12, 2022

(65) Prior Publication Data

US 2023/0110924 A1     Apr. 13, 2023

Related U.S. Application Data

(60) Provisional application No. 63/254,739, filed on Oct. 12, 2021.

(51) Int. Cl.
*A61B 5/1455*       (2006.01)
*A61B 5/1495*       (2006.01)
      (Continued)

(52) U.S. Cl.
CPC ........ *A61B 5/1495* (2013.01); *A61B 5/14551* (2013.01); *A61B 5/14552* (2013.01); *G16H 40/63* (2018.01); *A61B 5/145* (2013.01); *A61B*

*5/72* (2013.01); *A61B 2560/0223* (2013.01); *A61B 2562/02* (2013.01); *A61B 2562/0271* (2013.01)

(58) Field of Classification Search
CPC .............. A61B 5/1455; A61B 5/14551; A61B 5/14552; A61B 5/1495; A61B 5/0205
See application file for complete search history.

(56) References Cited

U.S. PATENT DOCUMENTS 5,522,389 A    6/1996   Fischer et al.
6,356,774 B1   3/2002   Bernstein et al.
      (Continued)

FOREIGN PATENT DOCUMENTS

WO      2011026053     8/2010

OTHER PUBLICATIONS

U.S. Appl. No. 16/857,695, by Covidien LP, filed Apr. 24, 2020.
(Continued)

*Primary Examiner* — Chu Chuan Liu
(74) *Attorney, Agent, or Firm* — Dymera IP, LLC

(57) ABSTRACT

A method for measuring oxygen saturation includes determining a difference in voltage value for a light emitting diode based on a first voltage at the light emitting diode for a first current and a second voltage at the light emitting diode for a second current and determining a temperature for the light emitting diode based on the difference in voltage value. The method further includes determining an intensity of a received photonic signal corresponding to an output photonic signal output using the light emitting diode and determining an oxygen saturation level based on the intensity of the received photonic signal and the temperature for the light emitting diode. The method further includes outputting an indication of the oxygen saturation level.

10 Claims, 8 Drawing Sheets

(51) Int. Cl.

| | |
|---|---|
| *G16H 40/63* | (2018.01) |
| *A61B 5/00* | (2006.01) |
| *A61B 5/145* | (2006.01) |

(56) References Cited

U.S. PATENT DOCUMENTS

| | | | |
|---|---|---|---|
| 7,120,480 B2 | 10/2006 | Chew et al. | |
| 7,343,186 B2 | 3/2008 | Lamego et al. | |
| 7,392,074 B2 | 6/2008 | Isaacson et al. | |
| 7,606,606 B2 | 10/2009 | Laakkonen | |
| 8,315,682 B2 | 11/2012 | Such et al. | |
| 8,401,605 B2 | 3/2013 | Huiku | |
| 8,515,514 B2 | 8/2013 | Huiku | |
| 8,720,249 B2 | 5/2014 | Al-Ali | |
| 8,740,808 B2 | 6/2014 | Curti et al. | |
| 8,781,544 B2 | 7/2014 | Al-Ali et al. | |
| 9,107,625 B2 | 8/2015 | Telfort et al. | |
| 9,125,606 B2 | 9/2015 | Verkruijsse et al. | |
| 9,157,773 B2 | 10/2015 | Joensuu | |
| 9,253,852 B2 | 2/2016 | Campbell et al. | |
| 9,265,456 B2 | 2/2016 | Kirenko et al. | |
| 9,341,565 B2 | 5/2016 | Lamego et al. | |
| 9,364,175 B2 | 6/2016 | Benni | |
| 9,404,961 B2 | 8/2016 | Gonopolskiy et al. | |
| 9,649,055 B2 | 5/2017 | Ashe et al. | |
| 9,651,632 B1 | 5/2017 | Knapp et al. | |
| 9,693,717 B2 | 7/2017 | Benni et al. | |
| 9,770,197 B2 | 9/2017 | Bresch et al. | |
| 9,770,213 B2 | 9/2017 | Kirenko et al. | |
| 9,801,556 B2 | 10/2017 | Kiani | |
| 9,839,381 B1 | 12/2017 | Weber et al. | |
| 9,861,317 B2 | 1/2018 | Ochs | |
| 9,980,650 B2 | 5/2018 | Bezemer | |
| 10,039,455 B2 | 8/2018 | Lading et al. | |
| 10,064,562 B2 | 9/2018 | Al-Ali | |
| 10,092,200 B2 | 10/2018 | Al-Ali et al. | |
| 10,123,726 B2 | 11/2018 | Al-Ali et al. | |
| 10,313,137 B2 | 6/2019 | Aarnio et al. | |
| 10,531,820 B2 | 1/2020 | De Haan et al. | |
| 10,646,167 B2 | 5/2020 | De Haan | |
| 10,849,538 B1 | 12/2020 | Meehan et al. | |
| 10,852,230 B1 | 12/2020 | Meehan | |
| 10,918,321 B2 | 2/2021 | Benni | |
| 10,993,644 B2 | 5/2021 | Huiku et al. | |
| 11,123,023 B2 | 9/2021 | Babaeizadeh | |
| 11,147,518 B1 | 10/2021 | Al-Ali et al. | |
| 11,202,582 B2 | 12/2021 | Verkruijsse et al. | |
| 11,519,850 B2 | 12/2022 | Meehan | |
| 11,564,630 B2 | 1/2023 | Huiku et al. | |
| 11,653,862 B2 | 5/2023 | Dalvi et al. | |
| 11,839,470 B2 | 12/2023 | Kiani et al. | |
| 2005/0250998 A1 | 11/2005 | Huiku | |
| 2007/0197885 A1 | 8/2007 | Mah et al. | |
| 2010/0145645 A1 | 6/2010 | Gonopolskiy et al. | |
| 2013/0336360 A1* | 12/2013 | Pauritsch | H05B 45/14 |
| | | | 374/163 |
| 2014/0275890 A1 | 9/2014 | Meehan et al. | |
| 2016/0354017 A1 | 12/2016 | Meehan et al. | |
| 2017/0273560 A1 | 9/2017 | Ballam et al. | |
| 2018/0235525 A1 | 8/2018 | Blanken | |
| 2018/0344227 A1 | 12/2018 | Cronin et al. | |
| 2018/0353111 A1 | 12/2018 | Buxton et al. | |
| 2019/0175030 A1 | 6/2019 | Verkruijsse et al. | |
| 2019/0209025 A1 | 7/2019 | Al-Ali | |
| 2020/0138349 A1 | 5/2020 | Lamminmaki et al. | |
| 2021/0219884 A1 | 7/2021 | De Haan | |
| 2023/0015851 A1 | 1/2023 | Verkruijsse et al. | |
| 2023/0125960 A1 | 4/2023 | Weber et al. | |
| 2023/0157578 A1 | 5/2023 | Crema | |

OTHER PUBLICATIONS

U.S. Appl. No. 17/082,944, filed Oct. 28, 2020, naming inventors Meehan et al.

U.S. Appl. No. 18/046,029, filed Oct. 12, 2022, naming inventors Reustle et al.

U.S. Appl. No. 18/046,096, filed. Oct. 12, 2022, naming inventors Taussig et al.

Welles et al., "Estimation of core body temperature from skin temperature, heat flux, and heart rate using a Kalman filter," Computers in Biology and Medicine, vol. 99, Aug. 1, 2018, 3 pp.

* cited by examiner

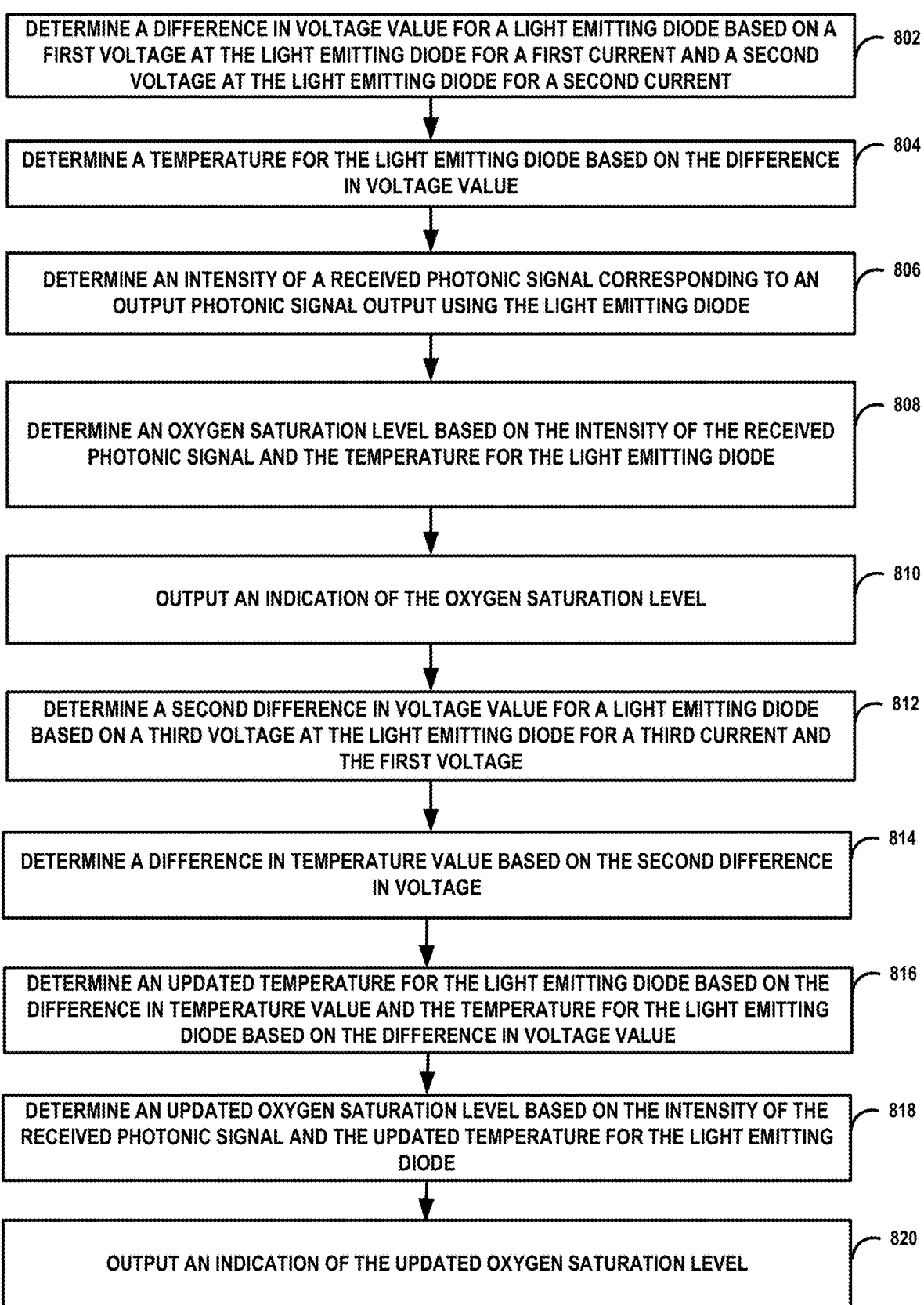

DETERMINE A DIFFERENCE IN VOLTAGE VALUE FOR A LIGHT EMITTING DIODE BASED ON A FIRST VOLTAGE AT THE LIGHT EMITTING DIODE FOR A FIRST CURRENT AND A SECOND VOLTAGE AT THE LIGHT EMITTING DIODE FOR A SECOND CURRENT — 802

DETERMINE A TEMPERATURE FOR THE LIGHT EMITTING DIODE BASED ON THE DIFFERENCE IN VOLTAGE VALUE — 804

DETERMINE AN INTENSITY OF A RECEIVED PHOTONIC SIGNAL CORRESPONDING TO AN OUTPUT PHOTONIC SIGNAL OUTPUT USING THE LIGHT EMITTING DIODE — 806

DETERMINE AN OXYGEN SATURATION LEVEL BASED ON THE INTENSITY OF THE RECEIVED PHOTONIC SIGNAL AND THE TEMPERATURE FOR THE LIGHT EMITTING DIODE — 808

OUTPUT AN INDICATION OF THE OXYGEN SATURATION LEVEL — 810

DETERMINE A SECOND DIFFERENCE IN VOLTAGE VALUE FOR A LIGHT EMITTING DIODE BASED ON A THIRD VOLTAGE AT THE LIGHT EMITTING DIODE FOR A THIRD CURRENT AND THE FIRST VOLTAGE — 812

DETERMINE A DIFFERENCE IN TEMPERATURE VALUE BASED ON THE SECOND DIFFERENCE IN VOLTAGE — 814

DETERMINE AN UPDATED TEMPERATURE FOR THE LIGHT EMITTING DIODE BASED ON THE DIFFERENCE IN TEMPERATURE VALUE AND THE TEMPERATURE FOR THE LIGHT EMITTING DIODE BASED ON THE DIFFERENCE IN VOLTAGE VALUE — 816

DETERMINE AN UPDATED OXYGEN SATURATION LEVEL BASED ON THE INTENSITY OF THE RECEIVED PHOTONIC SIGNAL AND THE UPDATED TEMPERATURE FOR THE LIGHT EMITTING DIODE — 818

OUTPUT AN INDICATION OF THE UPDATED OXYGEN SATURATION LEVEL — 820

FIG. 8

LIGHT EMITTING DIODE TEMPERATURE ESTIMATION

This application claims the benefit of U.S. Provisional Patent Application No. 63/254,739, filed 12 Oct. 2021, the entire contents of which is incorporated herein by reference.

TECHNICAL FIELD

This disclosure relates to determining blood oxygen saturation.

BACKGROUND

An oximeter may output small beams of light through blood and measure absorption values of the small beams of light to estimate oxygen saturation levels in the blood. For example, blood with relatively high oxygen saturation may absorb more light at a particular wavelength than blood with relatively low oxygen saturation. As such, the oximeter may determine that oxygen saturation levels in blood increase as less light at particular wavelengths is received after passing through the blood.

SUMMARY

In general, this disclosure relates to devices, systems, and techniques for determining a temperature of a sensor device of an oximeter. For example, a device may measure a diode voltage at a light emitting diode while applying different currents at the light emitting diode. The device may determine a temperature for the light emitting diode using the voltages measured while applying different currents. In this example, the device may cancel out the effects of resistance (e.g., from cables, connectors, circuit board traces, etc.) to determine a "true" temperature at the light emitting diode to help to ensure proper construction and/or accuracy of the sensor device. For instance, the device may verify, based on the temperature estimation utilizing light emitting diodes, whether the light emitting diodes' calibration information remains consistent after manufacturing, shipping, aging, etc. In this way, the device may be validated to help to ensure proper construction and/or accuracy of the sensor device before moving forward with correcting blood oxygen saturation values based on light emitting diodes' temperature estimations.

Moreover, in some examples, a system may track or update the temperature at the light emitting diode based on a change in voltage (e.g., a forward voltage). For example, the device may determine the temperature using the voltages measured while applying different currents. In this example, the device may determine a difference in a voltage value between a first voltage value at the light emitting diode when the temperature was previously determined and a third voltage value at the light emitting diode. In this example, the device may determine a difference in temperature value based on the difference in voltage value. For example, the device may multiply the difference in voltage value by a factor $$\left(\text{e.g., } \frac{\Delta T}{\Delta V}\right)$$

) to generate the difference in temperature value. The device may determine the updated temperature based on the difference in temperature value. For instance, the device may add the difference in temperature value to the temperature determined using the first voltage (e.g., a previously determined temperature). In this way, the system may drive the light emitting diode with a current selected to control an output of light emitted, which may allow for a temperature at the light emitting diode to be updated during an operation of the light emitting diode (e.g., while determining an oxygen saturation level).

In one example, a device for measuring oxygen saturation includes circuitry configured to determine a difference in voltage value for a light emitting diode based on a first voltage at the light emitting diode for a first current and a second voltage at the light emitting diode for a second current. The difference in voltage value is dependent on a temperature at the light emitting diode. The circuitry is further configured to determine a temperature for the light emitting diode based on the difference in voltage value. The circuitry is further configured to determine an intensity of a received photonic signal corresponding to an output photonic signal output using the light emitting diode. The circuitry is further configured to determine an oxygen saturation level based on the intensity of the received photonic signal and the temperature for the light emitting diode. The circuitry is further configured to output an indication of the oxygen saturation level.

In another example, a method for measuring oxygen saturation includes determining a difference in voltage value for a light emitting diode based on a first voltage at the light emitting diode for a first current and a second voltage at the light emitting diode for a second current. The method further includes determining a temperature for the light emitting diode based on the difference in voltage value. The method further includes determining an intensity of a received photonic signal corresponding to an output photonic signal output using the light emitting diode. The method further includes determining an oxygen saturation level based on the intensity of the received photonic signal and the temperature for the light emitting diode. The method further includes outputting an indication of the oxygen saturation level.

In one example, a system for measuring oxygen saturation includes a sensor device comprising a light emitting diode and oximetry device comprising circuitry. The oximetry device comprising circuitry is configured to determine a difference in voltage value for the light emitting diode based on a first voltage at the light emitting diode for a first current and a second voltage at the light emitting diode for a second current. The oximetry device comprising circuitry is further configured to determine a temperature for the light emitting diode based on the difference in voltage value and determine an intensity of a received photonic signal corresponding to an output photonic signal output using the light emitting diode. The oximetry device comprising circuitry is further configured to determine an oxygen saturation level based on the intensity of the received photonic signal and the temperature for the light emitting diode and output an indication of the oxygen saturation level.

In another example, a device for measuring oxygen saturation includes circuitry configured to determine a second difference in voltage value for the light emitting diode based on a third voltage at the light emitting diode for a third current and the first voltage and determine a difference in temperature value based on the second difference in voltage. The device is further configured to determine an updated temperature for the light emitting diode based on the difference in temperature value and the temperature for the light emitting diode based on the difference in voltage value.

In one example, a method for measuring oxygen satura-tion includes determining a second difference in voltage value for the light emitting diode based on a third voltage at the light emitting diode for a third current and the first voltage and determining a difference in temperature value based on the second difference in voltage. The method further includes determining an updated temperature for the light emitting diode based on the difference in temperature value and the temperature for the light emitting diode based on the difference in voltage value.

In another example, a system for measuring oxygen saturation includes a sensor device comprising a light emit-ting diode and oximetry device comprising circuitry. The oximetry device comprising circuitry is configured to deter-mine a second difference in voltage value for the light emitting diode based on a third voltage at the light emitting diode for a third current and the first voltage and determine a difference in temperature value based on the second difference in voltage. The circuitry is further configured to determine an updated temperature for the light emitting diode based on the difference in temperature value and the temperature for the light emitting diode based on the dif-ference in voltage value.

BRIEF DESCRIPTION OF THE DRAWINGS

FIG. 8 is a flow chart illustrating an example process of estimating temperature, in accordance with techniques described herein.

DETAILED DESCRIPTION

Figure 1:
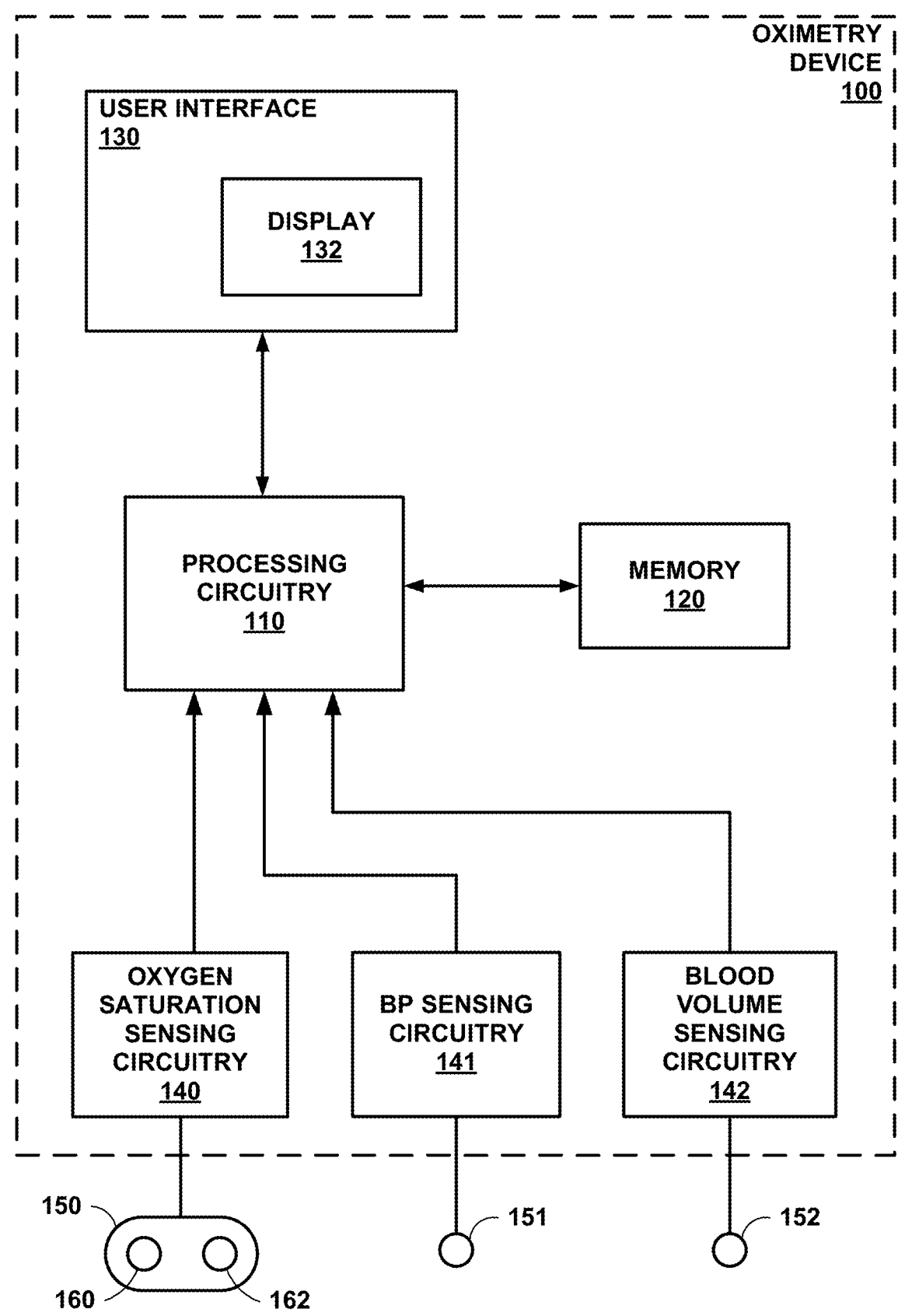
FIG. 1 is a conceptual block diagram illustrating an example oximetry device.

An oximeter may refer to a medical device configured to determine an oxygen saturation of an analyzed tissue. For purposes of this disclosure an oximeter may be defined as a device that measures other elements besides oxygenation. For example, an oximeter may measure other characteristics and chemical compositions of blood, like carbon monoxide. In other cases, an oximeter may only be used to measure the photoplesmograph of a subject for determination of pulse rate. Examples of an oximeter may include, for example, a pulse oximeter, a regional oximeter, a CO— oximeter, or another oximeter. A pulse oximeter may be configured to estimate arterial oxygen saturation of blood. A regional oximeter may be configured to estimate blood oxygen saturation in a region of a subject's (e.g., a human patient) tissue. For example, the regional oximeter may be config-ured to determine a differential absorption value for each of two or more wavelengths of light received at two different locations on the subject's body to estimate the regional blood oxygen saturation of hemoglobin in a region of the subject's tissue. For each wavelength of light, the regional oximeter may compare the amount of light absorbed by the subject's tissue in a first region to the amount of light absorbed by the subject's tissue in a second region to derive the differential absorption values. A sensor device may include a regional oximeter and a pulse oximeter.

An oximeter (e.g., a pulse oximeter, a regional oximeter, a CO— oximeter, etc.) may include a sensor device that is placed at a site on a patient, for example, on a fingertip, toe, forehead or earlobe, or in the case of a neonate, across a foot, across a hand, or another location. The oximeter may use a light source to pass light through blood perfused tissue and photoelectrically sense the absorption of the light in the tissue. Additional suitable sensor locations may include, for example, a neck to monitor carotid artery pulsatile flow, a wrist to monitor radial artery pulsatile flow, an inside of a patient's thigh to monitor femoral artery pulsatile flow, an ankle to monitor tibial artery pulsatile flow, around or in front of an ear, the cerebral cortex, locations with strong pulsatile arterial flow, or other locations.

The oximeter may be configured to output a photonic signal that interacts with tissue at one or more wavelengths that are attenuated by the blood in an amount representative of the blood constituent concentration. The oximeter may be configured to generate the photonic signal at red and infrared (IR) wavelengths. The oximeter may estimate the blood oxygen saturation of hemoglobin in arterial blood based on an intensity of the photonic signal at the red wavelength and the photonic signal at the infrared wavelength. While vari-ous examples described herein refer to a light emitting diode (LED) that may output relatively low intensity light, in some examples, LEDs may include devices that output relatively intense beams of light of infrared radiation (e.g., laser diodes, vertical-cavity surface-emitting lasers), or another device that emits light using at least one p-type junction and at least one n-type junction. Moreover, while examples described herein may refer to a device emitting light (e.g., LED, laser diode, etc.) similar techniques may be used with devices that receive light (e.g., photodiodes). Further, the number of diode devices could be one or more than one.

LEDs of an oximeter may have characteristics that impact the wavelength of light emitted, which may impact an accuracy of a determined oxygen saturation level. For example, a temperature may impact one or more physical characteristics (e.g., the wavelength of light emitted by the LED) and one or more intermediate variables that represents no "true" physical measurement but act as a temperature dependent variable of the LED.

An oximeter may estimate a wavelength of light emitted by a light emitting diode based on a diode voltage measured at the light emitting diode. The diode voltage may include a "true" forward voltage at the light emitting diode and other as voltages resulting from current flowing through a series resistance for the light emitting diode. This series resistance may include resistance from cables, external cables, con-nectors, traces, and other resistances in series with the light emitting diode. For example, the oximeter may measure the diode voltage across a positive terminal and a negative terminal of the oximeter, where current flows from the positive terminal through one or more cables (e.g., a cable, a cable and an extension cable, etc.) to the light emitting diode and from the light emitting diode through one or more cables to the negative terminal. However, the "true" forward voltage at a light emitting diode may be difficult to accurately measure. For instance, changes in a cable (e.g., from a 6 foot cable to a 10 foot cable) used to connect an oximeter device to a sensor device may significantly change a measured diode voltage, which may result in error in the estimated forward voltage. Moreover, the forward voltage may vary for different currents, which may result in approaches using Ohm's law and assuming a constant true forward voltage being inaccurate. As such, characteristics of the light emitting diode, such as, for example, but not limited to, a temperature at the light emitting diode, a wavelength of light emitted by the light emitting diode, and other characteristics that may be used to verify that LEDs used by the device are accurate and compatible with the device and/or improve a performance of the oximeter may be unavailable to the oximeter.

In accordance with the techniques of the disclosure, a device (e.g., an oximeter) may be configured to determine a temperature for the light emitting diode that accounts for the effects of a series resistance for a light emitting diode, which may increase an accuracy of the device in determining an oxygen saturation level. For example, the device may determine a difference in voltage value for a light emitting diode based on a first voltage at the light emitting diode for a first current and a second voltage at the light emitting diode for a second current. In this example, the device may determine a temperature for the light emitting diode based on the difference in voltage value and determine an intensity of a received photonic signal corresponding to an output photonic signal output using the light emitting diode. In this example, the device may determine an oxygen saturation level based on the intensity of the received photonic signal and the temperature for the light emitting diode and output an indication of the oxygen saturation level.

A device (e.g., an oximeter) may be configured to determine whether the temperature estimations between two LEDs match for a confidence metric or verification of the temperature. For example, if the temperature for a red LED calculated using techniques described herein and the temperature for an infrared LED calculated using techniques described herein are within a certain tolerance, then the device may determine a relatively high confidence metric for the temperatures at the red LED and the infrared LED. If the temperature for the red LED calculated using techniques described herein and the temperature for the infrared LED calculated using techniques described herein are not within the certain tolerance, then the device may determine a relatively low confidence metric for the temperatures at the red LED and the infrared LED.

The device may use the temperature for the light emitting diode to estimate a temperature of a die for the light emitting diode, which may be used to help to ensure that the sensor device is operating within a target range of operating temperatures. In some examples, when the difference in red LED temperature estimations and infrared LED temperature estimations are within a set tolerance, the device may apply wavelength compensation to account for a temperature at the die of the light emitting diode, which may improve an accuracy of measurements (e.g., an oxygen saturation level, blood oxygen saturation (SpO2), etc.) performed by the oximetry device.

More specifically, light emitting diodes of a sensor device may be manufactured to output a photonic signal at a particular wavelength with a manufacturing tolerance. For example, a first LED may output a first phonic signal (e.g., red light) at a first wavelength range (e.g., 630 nm-700 nm) with a first manufacturing tolerance of 5%. In this example, a second LED may output a second phonic signal (e.g., infrared light) at a second wavelength range (e.g., 700 nm-1200 nm) with a second manufacturing tolerance of 5%.

To account for the manufacturing tolerances, some oximeters may use calibration information that are established for each sensor. For example, some oximeters may be configured to store calibration information about LEDs of the oximeter in memory (e.g., EEPROM). The calibration information may help to account for manufacturing tolerances of the LEDs, which can shift wavelength(s) of light emitted by the LEDs. However, changes in temperature may significantly impact a wavelength emitted by a light emitting diode, particularly, light emitting diodes that emit red light, which may shift a few nanometers within an operating range of between 0° C. and 40° C. In accordance with the techniques of the disclosure, a device may estimate a temperature at the light emitting diode and determine a wavelength of light emitted by a light emitting diode based on the temperature at the light emitting diode. For example, the device may determine a temperature for the light emitting diode based on a difference in voltage value for a light emitting diode based on a first voltage at the light emitting diode for a first current and a second voltage at the light emitting diode for a second current. In some examples, the device may skip the wavelength estimate and use temperature dependent calibration slopes. For example, the device may use temperature information to directly correct for calibration error by correcting the calibration coefficients and/or by adjusting the signal level (e.g., using a ratio of ratios (ratrat), etc.). For instance, the device may apply a correction to a ratio of a detected pulsatile signal to a non-pulsatile signal from the red LED to a detected pulsatile signal to a non-pulsatile signal from the infrared LED. In some examples, the device may use the difference in voltage value and directly apply a calibration correction. In this way, techniques described herein may account for temperature at the light emitting diode die, which may improve an accuracy of the oximetry in performing an SpO2 measurement and/or other measurements.

FIG. 1 is a conceptual block diagram illustrating an example oximetry device 100. Oximetry device 100 may comprise, for example, a regional oximetry device, a pulse oximetry device, a co-oximeter device, or another oximeter device. Oximetry device 100 includes processing circuitry 110, memory 120, user interface 130, display 132, sensing circuitry 140, 141, and 142, and sensing device(s) 150, 151, and 152. In some examples, oximetry device 100 may be configured to determine and display the cerebral autoregulation status of a patient, e.g., during a medical procedure or for more long-term monitoring, such as monitoring of prenatal infants, children, or adults. A clinician may receive information regarding the cerebral autoregulation status of a patient via display 132 and adjust treatment or therapy to the patient based on the cerebral autoregulation status information. Although oximetry device 100 is described as an example device herein, other devices may calculate blood pressure and/or use blood pressure for other physiological monitoring and perform a similar compensation process on blood pressures subjected to abrupt changes in the measured blood pressure values.

Processing circuitry 110 as well as other processors, processing circuitry, controllers, control circuitry, and the like, described herein, may include one or more processors.

Processing circuitry 110 may include any combination of integrated circuitry, discrete logic circuitry, analog circuitry, such as one or more microprocessors, digital signal processors (DSPs), application specific integrated circuits (ASICs), or field-programmable gate arrays (FPGAs). In some examples, processing circuitry 110 may include multiple components, such as any combination of one or more microprocessors, one or more DSPs, one or more ASICs, or one or more FPGAs, as well as other discrete or integrated logic circuitry, and/or analog circuitry.

Memory 120 may be configured to store measurements of blood pressure, oxygen saturation, blood volume, other physiological parameters, relationships between blood pressure and physiological parameters, MAP values, rSO2 values, COx values, BVS values, HVx values, and/or value(s) of a limit of autoregulation (LLA) and/or an upper limit of autoregulation (ULA), for example. Memory 120 may also be configured to store data such as thresholds for detecting abrupt changes in blood pressure, previous LLA and ULA values, and/or other physiological parameters and expected values of physiological parameters. Memory 120 may also be configured to store data such as threshold levels for physiological parameters, threshold values for blood pressure, and/or threshold levels for signal quality metrics. The thresholds or other data may stay constant throughout the use of device 100 and across multiple patients, or these values may change over time. Memory 120 may store calibrated values. Examples of calibrated values may include, but are not limited to, one or more of a calibration temperature for a light emitting diode, the slope factor for the light emitting diode, and the calibration difference in voltage value for the light emitting diode 460A, and/or another value. Part of or all of memory 120 may be located in sensor 150. For example, a memory of sensor 150 may store one or more of a calibration temperature for a light emitting diode, the slope factor for the light emitting diode, and the calibration difference in voltage value for the light emitting diode 460A, and/or another value.

Memory 120 or sensor 150 may store program instructions, which may include one or more program modules, which are executable by processing circuitry 110. When executed by processing circuitry 110, such program instructions may cause processing circuitry 110 to provide the functionality ascribed to it herein. For example, memory 120 may store instructions regarding how to determine abrupt changes in measured blood pressure, calculating ULA and LLA values, and presenting information to the user via user interface 130. The program instructions may be embodied in software, firmware, and/or RAMware. Memory 120, as well as other memory devices described herein (e.g., memory 220 shown in FIG. 2), may include any volatile, non-volatile, magnetic, optical, circuitry, or electrical media, such as a random access memory (RAM), read-only memory (ROM), non-volatile RAM (NVRAM), electrically-erasable programmable ROM (EEPROM), flash memory, or any other digital media.

User interface 130 and/or display 132 may be configured to present information to a user (e.g., a clinician). User interface 130 and/or display 132 may be configured to present a graphical user interface to a user, where each graphical user interface may include indications of values of one or more physiological parameters of a subject. For example, processing circuitry 110 may be configured to present blood pressure values, other physiological parameter values (e.g., heart rate), and indications of cerebral autoregulation status of a patient via display 132. In some examples, if processing circuitry 110 determines that the cerebral autoregulation status of the patient is impaired, then processing circuitry 110 may present a notification (e.g., an alert) indicating the impaired cerebral autoregulation status via display 132. As another example, processing circuitry 110 may present, via display 132, estimates of regional oxygen saturation (rSO2) for a patient, an estimate of the blood oxygen saturation (SpO2) determined by processing circuitry 110, pulse rate information, respiration rate information, blood pressure, any other patient parameters, or any combination thereof.

User interface 130 and/or display 132 may include a monitor, cathode ray tube display, a flat panel display such as a liquid crystal (LCD) display, a plasma display, or a light emitting diode (LED) display, personal digital assistant, mobile phone, tablet computer, laptop computer, any other suitable display device, or any combination thereof. User interface 130 may also include means for projecting audio to a user, such as speaker(s). Processing circuitry 110 may be configured to present, via user interface 130, a visual, audible, or somatosensory notification (e.g., an alarm signal) indicative of the patient's autoregulation status. User interface 130 may include or be part of any suitable device for conveying such information, including a computer workstation, a server, a desktop, a notebook, a laptop, a handheld computer, a mobile device, or the like. In some examples, processing circuitry 110 and user interface 130 may be part of the same device or supported within one housing (e.g., a computer or monitor).

Sensing circuitry 140, 141, and 142 may be configured to receive physiological signals sensed by respective sensing device(s) 150, 151, and 152 and communicate the physiological signals to processing circuitry 110. Sensing device (s) 150, 151, and 152 may include any sensing hardware configured to sense a physiological parameter of a patient, such as, but not limited to, one or more electrodes, optical receivers, blood pressure cuffs, or the like. Sensing circuitry 140, 141, and 142 may convert the physiological signals to usable signals for processing circuitry 110, such that processing circuitry 110 is configured to receive signals generated by sensing circuitry 140, 141, and 142. Sensing circuitry 140, 141, and 142 may receive signals indicating physiological parameters from a patient, such as, but not limited to, blood pressure, regional oxygen saturation, heart rate, and respiration. Sensing circuitry 140, 141, and 142 may include, but are not limited to, blood pressure sensing circuitry, oxygen saturation sensing circuitry, heart rate sensing circuitry, temperature sensing circuitry, electrocardiography (ECG) sensing circuitry, electroencephalogram (EEG) sensing circuitry, or any combination thereof. In some examples, sensing circuitry 140, 141, and 142 and/or processing circuitry 110 may include signal processing circuitry such as an analog-to-digital converter. Blood pressure (BP) sensing circuitry 141 may comprise multi-parameter sensing circuitry that includes, for example, blood pressure circuitry and plethysmography (PPG) circuitry.

Oxygen saturation sensing device 150 is a regional or arterial oxygen saturation sensor configured to generate an oxygen saturation signal indicative of blood oxygen saturation within the venous, arterial, and/or capillary systems within a region of the patient. For example, oxygen saturation sensing device 150 may be configured to be placed on the patient's forehead and may be used to determine the oxygen saturation of the patient's blood within the venous, arterial, and/or capillary systems of a region underlying the patient's forehead (e.g., in the cerebral cortex).

Oxygen saturation sensing device 150 may include emitter 160 and detector 162. Emitter 160 may include at least two light emitting diodes (LEDs), each configured to emit at different wavelengths of light, e.g., red or near infrared light. In some examples, light drive circuitry (e.g., within sensing device 150, sensing circuitry 140, and/or processing circuitry 110) may provide a light drive signal to drive emitter 160 and to cause emitter 160 to emit light. In some examples, the LEDs of emitter 160 emit light in the wavelength range of about 600 nanometers (nm) to about 1000 nm. In a particular example, one LED of emitter 160 is configured to emit light at a wavelength of about 730 nm and the other LED of emitter 160 is configured to emit light at a wavelength of about 810 nm. Other wavelengths of light may also be used in other examples.

Detector 162 may include a first detection element positioned relatively "close" (e.g., proximal) to emitter 160 and a second detection element positioned relatively "far" (e.g., distal) from emitter 160 (these multiple detectors are shown as a single detector in the example of FIG. 1). Light intensity of multiple wavelengths may be received at both the "close" and the "far" detector 162. For example, if two wavelengths are used, the two wavelengths may be contrasted at each location and the resulting signals may be contrasted to arrive at a regional or arterial saturation value that pertains to additional tissue through which the light received at the "far" detector passed (tissue in addition to the tissue through which the light received by the "close" detector passed, e.g., the brain tissue), when it was transmitted through a region of a patient (e.g., a patient's cranium). Surface data from the skin and skull may be subtracted out, to generate a regional or arterial oxygen saturation signal for the target tissues over time. Oxygen saturation sensing device 150 may provide the regional or arterial oxygen saturation signal to processing circuitry 110 or to any other suitable processing device to enable evaluation of the patient's autoregulation status.

Blood pressure sensing device 151 and oxygen saturation sensing device 150 may each be placed on the same or different parts of the patient's body. For example, blood pressure sensing device 151 and oxygen saturation sensing device 150 may physically separate from each other and be separately placed on the patient. As another example, blood pressure sensing device 151 and oxygen saturation sensing device 150 may in some cases be part of the same sensor or supported by a single sensor housing. For example, blood pressure sensing device 151 and oxygen saturation sensing device 150 may be part of an integrated oximetry system configured to non-invasively measure blood pressure (e.g., based on time delays in a PPG signal) and regional or arterial oxygen saturation. One or both of blood pressure sensing device 151 or oxygen saturation sensing device 150 may be further configured to measure other parameters, such as hemoglobin, respiratory rate, respiratory effort, heart rate, saturation pattern detection, response to stimulus such as bispectral index (BIS) or electromyography (EMG) response to electrical stimulus, or the like. While an example oximetry device 100 is shown in FIG. 1, the components illustrated in FIG. 1 are not intended to be limiting. Additional or alternative components and/or implementations may be used in other examples.

Blood pressure sensing device 151 may be any sensor or device configured to obtain the patient's blood pressure (e.g., arterial blood pressure). In one example, the blood pressure sensing device 151 may include or be connected to a probe configured to be inserted into a blood pressure of the patient. In another example, blood pressure sensing device 151 may include a blood pressure cuff for non-invasively monitoring blood pressure or an arterial line for invasively monitoring blood pressure (e.g., a pressure probe configured to be placed within an artery or vein). In certain examples, blood pressure sensing device 151 may include one or more pulse oximetry sensors. In some such cases, the patient's blood pressure may be derived by processing time delays between two or more characteristic points within a single plethysmography (PPG) signal obtained from a single pulse oximetry sensor.

Processing circuitry 110 may be configured to receive one or more physiological signals generated by sensing devices 150, 151, and 152 and sensing circuitry 140, 141, and 142. The physiological signals may include a signal indicating blood pressure, a signal indicating oxygen saturation, and/or a signal indicating blood volume of a patient. Processing circuitry 110 may be configured to determine a relationship between blood pressure values of the patient and a physiological parameter of the patient, such as a correlation index (e.g., COx, a hemoglobin volume index (HVx)), an oxygen saturation value, a blood volume value, a gradient-based metric of two or more physiological parameters, and/or another physiological parameter. Processing circuitry 110 can determine a gradients-based metric by determining respective gradients of signals for physiological parameters and determining whether the respective gradients trend together.

In accordance with the techniques of the disclosure, a device such as oximetry device 100 may include voltage measuring circuitry (e.g., within sensing device 150, sensing circuitry 140, and/or processing circuitry 110) that is configured to determine a temperature for the light emitting diode that may reduce or eliminate the effects of a series resistance for a light emitting diode of emitter 160, which may increase an accuracy of the device in determining an oxygen saturation level. For example, the device may determine a difference in voltage value for the light emitting diode based on a first voltage at the light emitting diode for a first current and a second voltage at the light emitting diode for a second current. In this example, the device may determine a temperature for the light emitting diode based on the difference in voltage value and determine an intensity of a received photonic signal corresponding to an output photonic signal output using the light emitting diode. In this example, the device may determine an oxygen saturation level based on the intensity of the received photonic signal and the temperature for the light emitting diode and output an indication of the oxygen saturation level.

Processing circuitry 110 may be configured to verify (e.g., validate) that the LEDs used by the device for determining blood oxygen saturation values conform to the stored calibration information (e.g., are within the range defined by the calibration information). The validation of the LEDs to the calibration information may indicate that the LEDs are verified to be used for determining oxygen levels (e.g., measurements should be accurate). Moreover, the device may determine that emitter 160 is not safe when the temperature for one or more of the light emitting diodes is greater or less than a safe temperature threshold.

Processing circuitry 110 may, in response to determining that one or more light emitting diodes and/or one or more photodiodes are valid, determine an intensity of a received photonic signal corresponding to an output photonic signal output using the light emitting diode. For example, processing circuitry 110 may drive the light emitting diode to output the output photonic signal towards a subject's tissue and receive, from a detector (e.g., one or more photodiodes), the received photonic signal after the output photonic signal transmits through the subject's tissue.

Processing circuitry 110 may determine an oxygen saturation level based on the intensity of the received photonic signal and the temperature. For example, processing circuitry 110 may estimate a wavelength for an output photonic signal based on the temperature at the light emitting diode. In this example, processing circuitry 110 may determine the oxygen saturation level based on the estimated wavelength for the output photonic signal and the intensity of the received photonic signal.

In some examples, processing circuitry 110 may track or update the temperature at light emitting diode of emitter 160 based on a change in voltage (e.g., a forward voltage). For example, processing circuitry 110 may determine the temperature using the voltages measured while applying different currents. In this example, processing circuitry 110 may determine a difference in a voltage value between a first voltage value at the light emitting diode when the temperature was previously determined and a third voltage value at the light emitting diode of emitter 160. In this example, processing circuitry 110 may determine a difference in temperature value based on the difference in the voltage value. For example, processing circuitry 110 may multiply the difference in the voltage value by a factor $$\left(\text{e.g., } \frac{\Delta T}{\Delta V}\right)$$

to generate the difference in temperature value. The factor may be pre-loaded or dynamically determined. Processing circuitry 110 may determine the updated temperature based on the difference in temperature value. For instance, processing circuitry 110 may add the difference in temperature value to the temperature determined using the first voltage (e.g., a previously determined temperature). In this way, processing circuitry 110 may drive the light emitting diode of emitter 160 with a current selected to control an output of light emitted, which may allow for a temperature at the light emitting diode to be updated during an operation of the light emitting diode of emitter 160 (e.g., while determining an oxygen saturation level).

In the above examples, processing circuitry 110, light drive circuitry, and voltage measuring circuitry are described as performing the example techniques, wherein light drive circuitry and voltage measurement circuitry may be part of processing circuitry 110, sensing device 150 and/or sensing circuitry 140). However, any one or combination of processing circuitry 110, sensing circuitry 140, and/or sensing device 150 may be configured to perform the example techniques. For instance, the example techniques may be performed by circuitry, and example of the circuitry includes any one or any combination of processing circuitry 110, sensing circuitry 140, and/or sensing device 150.

Figure 2:
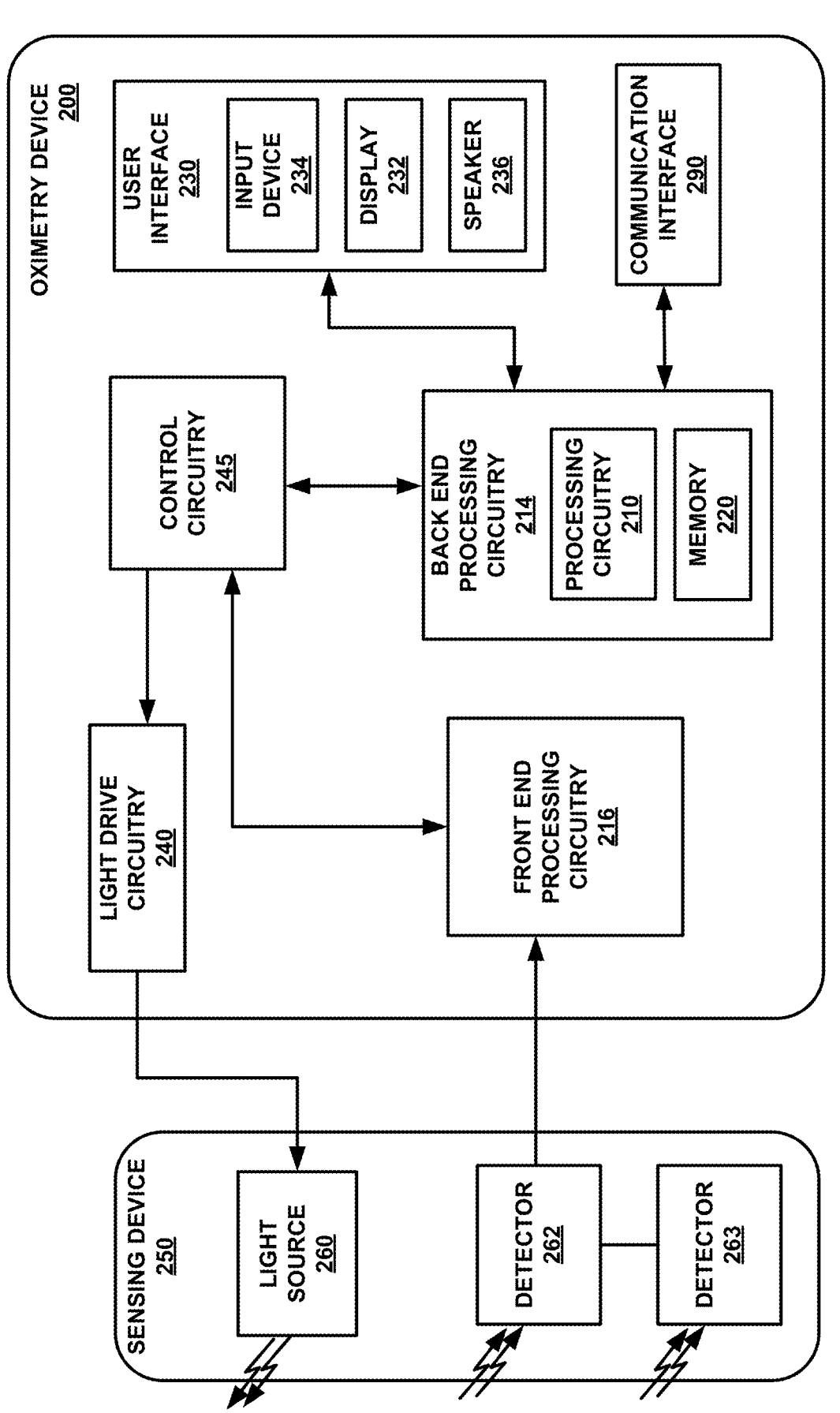
FIG. 2 is a conceptual block diagram illustrating an example oximetry device configured to monitor an auto-regulation status of a patient.

FIG. 2 is a conceptual block diagram illustrating an example oximetry device 200 configured to monitor the autoregulation status of a patient. Oximetry device 100 may comprise, for example, a regional oximetry device, a pulse oximetry device, a co-oximeter device, or another oximeter device. In the example shown in FIG. 2, oximetry device 200 is coupled to sensing device 250 and may be collectively referred to as a regional oximetry system, which each generate and process physiological signals of a subject. In some examples, sensing device 250 and oximetry device 200 may be part of an oximeter. Oximetry device 200 and sensing device 250 may be examples of oximetry device 100 and sensing device 150, respectively, of FIG. 1. As shown in

12

FIG. 2, oximetry device 200 includes back-end processing circuitry 214, user interface 230, light drive circuitry 240, front-end processing circuitry 216, control circuitry 245, and communication interface 290. Oximetry device 200 may be communicatively coupled to sensing device 250. Oximetry device 200 is an example of oximetry device 100 shown in FIG. 1. In some examples, oximetry device 200 may also include a blood pressure sensor and/or a blood volume sensor (e.g., sensing devices 151 and 152 of FIG. 1).

In the example shown in FIG. 2, sensing device 250 includes light source 260, detector 262, and detector 263. Light source 260 may be an example of emitter 160 of FIG. 1. Detectors 262 and 263 may be examples of detector 162 of FIG. 1. In some examples, sensing device 250 may include more than two detectors. Light source 260 may be configured to emit photonic signals having two or more wavelengths (e.g., up to four or more wavelengths, more than 4 wavelengths, etc.) of light (e.g., red and infrared (IR), or another wavelength of light) into a subject's tissue. For example, light source 260 may include a red light emitting light source and an IR light emitting light source, (e.g., red LED and an IR LED), for emitting light into the tissue of a subject to generate physiological signals. In some examples, the red wavelength may be between about 600 nm and about 700 nm, and the IR wavelength may be between about 800 nm and about 1000 nm. Other wavelengths of light may be used in other examples. Light source 260 may include any number of light sources with any suitable characteristics. In examples in which an array of sensors is used in place of sensing device 250, each sensing device may be configured to emit a single wavelength. For example, a first sensing device may emit only a red light while a second sensing device may emit only an IR light. In some examples, light source 260 may be configured to emit two or more wavelengths of near-infrared light (e.g., wavelengths between 600 nm and 1000 nm) into a subject's tissue. In some examples, light source 260 may be configured to emit four wavelengths of light (e.g., 724 nm, 770 nm, 810 nm, and 850 nm) into a subject's tissue. In some examples, the subject may be a medical patient.

As used herein, the term "light" may refer to energy produced by radiative sources and may include one or more of ultrasound, radio, microwave, millimeter wave, infrared, visible, ultraviolet, gamma ray or X-ray electromagnetic radiation. Light may also include any wavelength within the radio, microwave, infrared, visible, ultraviolet, or X-ray spectra, and that any suitable wavelength of electromagnetic radiation may be appropriate for use with the present techniques. Detectors 262 and 263 may be chosen to be specifically sensitive to the chosen targeted energy spectrum of light source 260.

Detectors 262 and 263 may be configured to detect the intensity of multiple wavelengths of near-infrared light. In some examples, detectors 262 and 263 may be configured to detect the intensity of light at the red and IR wavelengths. In some examples, an array of detectors may be used and each detector in the array may be configured to detect an intensity of a single wavelength. In operation, light may enter detector 262 after passing through the subject's tissue, including skin, bone, and other shallow tissue (e.g., non-cerebral tissue and shallow cerebral tissue). Light may enter detector 263 after passing through the subject's tissue, including skin, bone, other shallow tissue (e.g., non-cerebral tissue and shallow cerebral tissue), and deep tissue (e.g., deep cerebral tissue). Detectors 262 and 263 may convert the intensity of the received light into an electrical signal. The light intensity may be directly related to the absorbance and/or reflectance of light in the tissue. That is, when more light at a certain wavelength is absorbed or reflected, less light of that wavelength is received from the tissue by detectors 262 and 263.

Detector 262 and/or detector 263 may determine a first intensity of a first received photonic signal corresponding to a first output photonic signal (e.g., red light) output using a light emitting diode of light source 260. More specifically, processing circuitry (e.g., light drive circuitry 240) may be configured to drive the light emitting diode of light source 260 to output the output photonic signal towards a subject's tissue and receive, from detector 262 and/or detector 263, the first received photonic signal after the output photonic signal transmits through the subject's tissue.

After converting the received light to an electrical signal, detectors 262 and 263 may send the detection signals to oximetry device 200, which may process the detection signals and determine physiological parameters (e.g., based on the absorption of the red and IR wavelengths in the subject's tissue and transmittance of red and IR wavelengths to both detectors). For example, oximetry device 200 may determine an oxygen saturation level based on the intensity of the received photonic signal. More specifically, processing circuitry 210 may estimate a wavelength for the output photonic signal based on a temperature at a light emitting diode (e.g., a red light emitting diode, an infrared light emitting diode, etc.). For instance, processing circuitry 210 may estimate the wavelength for the output photonic signal as equal to a wavelength identified in calibration information stored in memory 220 that corresponds to the temperature at the light emitting diode.

Processing circuitry 210 may determine the oxygen saturation level based on the wavelength for the output photonic signal and the intensity of the received photonic signal. For example, processing circuitry 210 may determine the oxygen saturation level by matching an amount of absorption of light at a particular wavelength (e.g., a difference in magnitude between an emitted light and a received light) with a table entry stored in memory 220 and output a corresponding oxygen saturation level for the absorption of light at the particular wavelength. For instance, processing circuitry 210 may determine the oxygen saturation level by matching a first amount of absorption of light at a first wavelength (e.g., red light) and a second amount of absorption of light at a second wavelength (e.g., infrared light) with a table entry stored in memory 220 and outputting a corresponding oxygen saturation level.

One or more of the detection signals may be preprocessed by sensing device 250 before being transmitted to oximetry device 200. Additional example details of determining oxygen saturation based on light signals may be found in commonly assigned U.S. Pat. No. 9,861,317, which issued on Jan. 9, 2018, and is entitled "Methods and Systems for Determining Regional Blood Oxygen Saturation," the entire content of which is incorporated herein by reference.

Control circuitry 245 may be coupled to light drive circuitry 240, front-end processing circuitry 216, and back-end processing circuitry 214, and may be configured to control the operation of these components. In some examples, control circuitry 245 may be configured to provide timing control signals to coordinate their operation. For example, light drive circuitry 240 may generate one or more light drive signals, which may be used to turn on and off light source 260, based on the timing control signals provided by control circuitry 245. Front-end processing circuitry 216 may use the timing control signals to operate synchronously with light drive circuitry 240. For example, front-end processing circuitry 216 may synchronize the operation of an analog-to-digital converter and a demultiplexer with the light drive signal based on the timing control signals. In addition, the back-end processing circuitry 214 may use the timing control signals to coordinate its operation with front-end processing circuitry 216.

Light drive circuitry 240, as discussed above, may be configured to generate a light drive signal that is provided to light source 260 of sensing device 250. The light drive signal may, for example, control the intensity of light source 260 and the timing of when light source 260 is turned on and off. In some examples, light drive circuitry 240 provides one or more light drive signals to light source 260. Where light source 260 is configured to emit two or more wavelengths of light, the light drive signal may be configured to control the operation of each wavelength of light. The light drive signal may comprise a single signal or may comprise multiple signals (e.g., one signal for each wavelength of light).

Front-end processing circuitry 216 may perform any suitable analog conditioning of the detector signals. The conditioning performed may include any type of filtering (e.g., low pass, high pass, band pass, notch, or any other suitable filtering), amplifying, performing an operation on the received signal (e.g., taking a derivative, averaging), performing any other suitable signal conditioning (e.g., converting a current signal to a voltage signal), or any combination thereof. The conditioned analog signals may be processed by an analog-to-digital converter of circuitry 216, which may convert the conditioned analog signals into digital signals. Front-end processing circuitry 216 may operate on the analog or digital form of the detector signals to separate out different components of the signals. Front-end processing circuitry 216 may also perform any suitable digital conditioning of the detector signals, such as low pass, high pass, band pass, notch, averaging, or any other suitable filtering, amplifying, performing an operation on the signal, performing any other suitable digital conditioning, or any combination thereof. Front-end processing circuitry 216 may decrease the number of samples in the digital detector signals. In some examples, front-end processing circuitry 216 may also remove dark or ambient contributions to the received signal.

Back-end processing circuitry 214 may include processing circuitry 210 and memory 220. Processing circuitry 210 may include an assembly of analog or digital electronic components and may be configured to execute software, which may include an operating system and one or more applications, as part of performing the functions described herein with respect to, e.g., processing circuitry 110 of FIG. 1. Processing circuitry 210 may receive and further process physiological signals received from front-end processing circuitry 216. For example, processing circuitry 210 may determine one or more physiological parameter values based on the received physiological signals. For example, processing circuitry 210 may compute one or more of regional oxygen saturation, blood oxygen saturation (e.g., arterial, venous, or both), pulse rate, respiration rate, respiration effort, blood pressure, hemoglobin concentration (e.g., oxygenated, deoxygenated, and/or total), any other suitable physiological parameters, or any combination thereof.

Processing circuitry 210 may perform any suitable signal processing of a signal, such as any suitable band-pass filtering, adaptive filtering, closed-loop filtering, any other suitable filtering, and/or any combination thereof. Processing circuitry 210 may also receive input signals from additional sources not shown. For example, processing circuitry 210 may receive an input signal containing information about treatments provided to the subject from user interface 230. Additional input signals may be used by processing circuitry 210 in any of the determinations or operations it performs in accordance with back-end processing circuitry 214 or oximetry device 200.

Processing circuitry 210 is an example of processing circuitry 110 and is configured to perform the techniques of this disclosure. For example, processing circuitry 210 may determine a difference in voltage value for a light emitting diode of light source 260 based on a first voltage at the light emitting diode for a first current and a second voltage at the light emitting diode for a second current. In this example, processing circuitry 210 may determine a temperature for the light emitting diode based on the difference in voltage value and determine an intensity of a received photonic signal corresponding to an output photonic signal output using the light emitting diode. In this example, processing circuitry 210 may determine an oxygen saturation level based on the intensity of the received photonic signal and the temperature for the light emitting diode and output an indication of the oxygen saturation level.

Processing circuitry 210 may be configured to verify (e.g., validate) that sensing device 250 conforms to the stored calibration information (e.g., are within the range defined by the calibration information) stored in memory 220. For example, processing circuitry 210 may determine that a light emitting diode of light source 260 is valid for temperature estimation use in response to determining that the temperature calculated for a red LED of light source 260 corresponds to (e.g., matches, is within a predetermined threshold, etc.) the temperature calculated for an infrared LED of light source 260.

Processing circuitry 210 may be configured to determine an oxygen saturation level using the light emitting diode of light source 260 and/or the photodiode of detector 262 and/or the photodiode of detector 263 in response to the determination that sensing device 250 is valid for temperature estimation use. For example, processing circuitry 210 may determine an intensity of a received photonic signal corresponding to an output photonic signal output using a light emitting diode of light source 260 and a photodiode of detector 262 (and/or a photodiode of detector 263). For example, light drive circuitry 240 may drive the light emitting diode to output the output photonic signal towards a subject's tissue and receive, from the photodiode, the received photonic signal after the output photonic signal transmits through the subject's tissue.

Processing circuitry 210 may determine an oxygen saturation level based on the intensity of the received photonic signal and the temperature of the LED at light source 260. For example, processing circuitry 210 may estimate a wavelength for an output photonic signal based on the temperature at the light emitting diode. In this example, processing circuitry 210 may determine the oxygen saturation level based on the estimated wavelength for the output photonic signal and the intensity of the received photonic signal.

Processing circuitry 210 may output an indication of the oxygen saturation level. For example, processing circuitry 210 may store an indication of the oxygen saturation level (e.g., a numerical value indicating the oxygen saturation level) for storage at memory 220. Processing circuitry 210 may output an indication of the oxygen saturation level (e.g., a numerical value indicating the oxygen saturation level) to user interface 230 for output on display 232. Processing circuitry 210 may output an indication of the oxygen saturation level (e.g., a numerical value indicating the oxygen saturation level) to communication interface 290 for storage and/or output at one or more external or implanted devices.

Memory 220 may include any suitable computer-readable media capable of storing information that can be interpreted by processing circuitry 210. In some examples, memory 220 may store reference absorption curves, reference sets, determined values, such as blood oxygen saturation, pulse rate, blood pressure, fiducial point locations or characteristics, initialization parameters, any other determined values, or any combination thereof, in a memory device for later retrieval. Memory 220 may also store thresholds for detecting abrupt changes in blood pressure, and so on. Back-end processing circuitry 214 may be communicatively coupled with user interface 230 and communication interface 290.

During calibration of sensing device 250, device 200 or another device (e.g., a calibration device) may generate calibration information. For example, device 200 or a calibration device may generate calibration temperature for one or more light emitting diodes of light source 260, a slope factor for the one or more light emitting diodes of light source 260, and the calibration difference in voltage value for one or more light emitting diodes of light source 260. Memory 220 may store the calibration information. As used herein, calibration information may include information for accounting for manufacturing tolerances of light source 260, such as, for example, but not limited to, a wavelength output by light emitting diodes of light source 260.

User interface 230 may include input device 234, display 232, and speaker 236 in some examples. User interface 230 is an example of user interface 130 shown in FIG. 1, and display 232 is an example of display 132 shown in FIG. 1. User interface 230 may include, for example, any suitable device such as one or more medical devices (e.g., a medical monitor that displays various physiological parameters, a medical alarm, or any other suitable medical device that either displays physiological parameters or uses the output of back-end processing 214 as an input), one or more display devices (e.g., monitor, personal digital assistant (PDA), mobile phone, tablet computer, clinician workstation, any other suitable display device, or any combination thereof), one or more audio devices, one or more memory devices, one or more printing devices, any other suitable output device, or any combination thereof.

Input device 234 may include one or more of any type of user input device such as a keyboard, a mouse, a touch screen, buttons, switches, a microphone, a joystick, a touch pad, or any other suitable input device or combination of input devices. In other examples, input device 234 may be a pressure-sensitive or presence-sensitive display that is included as part of display 232. Input device 234 may also receive inputs to select a model number of sensing device 250 or blood pressure processing equipment. In some examples, processing circuitry 210 may determine the type of presentation for display 232 based on user inputs received by input device 234.

Figure 3:
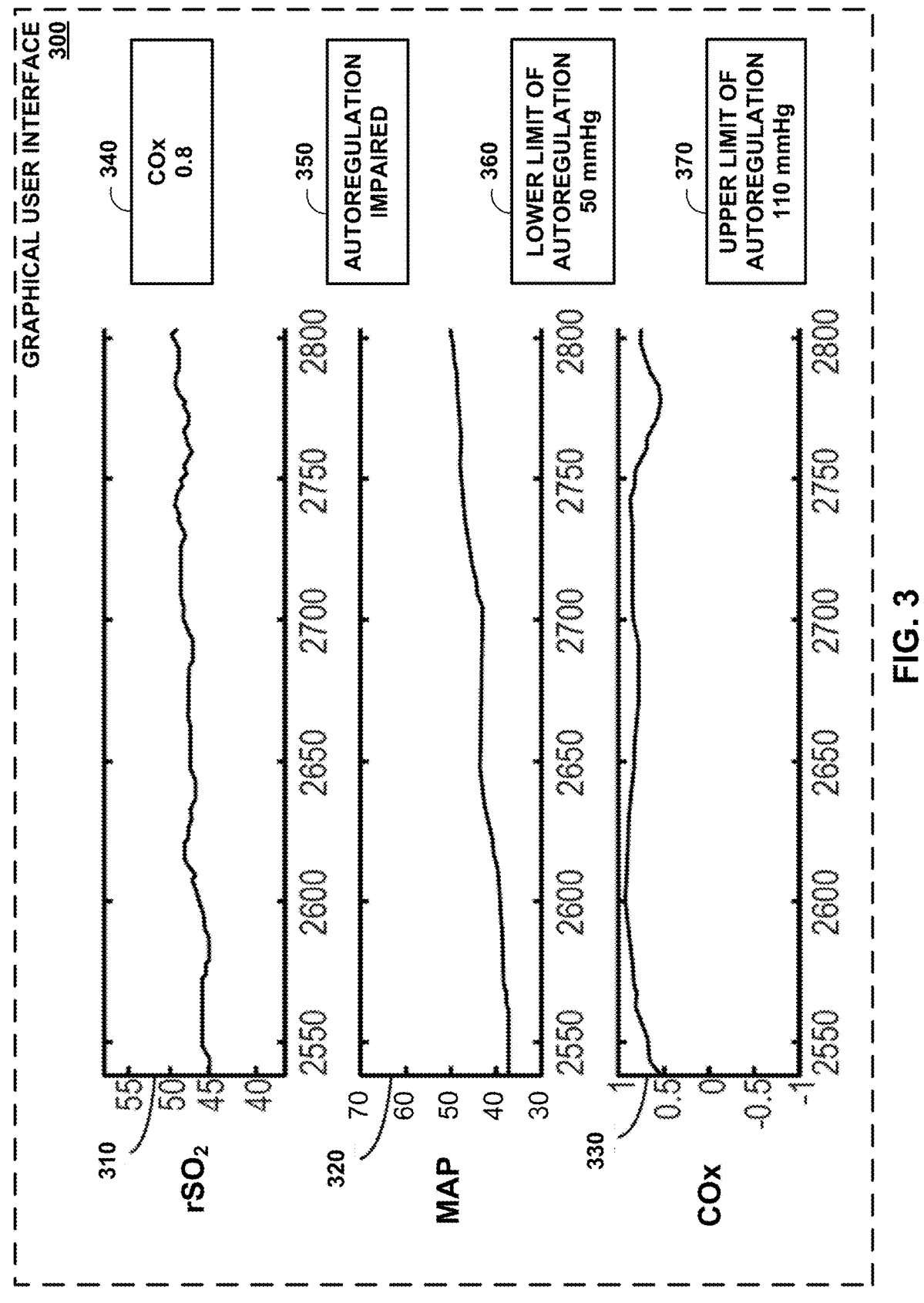
FIG. 3 is a conceptual diagram illustrating an example graphical user interface including autoregulation informa-tion presented on a display.

In some examples, the subject may be a medical patient, and display 232 may exhibit a list of values which may generally apply to the subject, such as, for example, an oxygen saturation signal indicator, a blood pressure signal indicator, a COx signal indicator, a COx value indicator, and/or an autoregulation status indicator. Display 232 may also be configured to present additional physiological parameter information. Graphical user interface 300 shown in FIG. 3 is an example of an interface that can be presented via display 232 of FIG. 2 under the control of processing circuitry 210. Additionally, display 232 may present, for example, one or more estimates of a subject's regional oxygen saturation generated by oximetry device 200 (referred to as an "rSO2" measurement). Display 232 may also present indications of the upper and lower limits of cerebral autoregulation. In some examples, user interface 230 includes speaker 236 that is configured to generate and provide an audible sound that may be used in various examples, such as for example, sounding an audible notification in the event that a patient's physiological parameters are not within a predefined normal range and/or in the event that processing circuitry 210 determines that sensed blood pressure values may be inaccurate due to a non-physiological reason such as due to movement of a blood pressure probe of blood pressure sensor device 151 (FIG. 1).

Communication interface 290 may enable oximetry device 200 to exchange information with other external or implanted devices. Communication interface 290 may include any suitable hardware, software, or both, which may allow oximetry device 200 to communicate with electronic circuitry, a device, a network, a server or other workstations, a display, or any combination thereof. For example, oximetry device 200 may receive MAP (or other measured blood pressure) values and/or oxygen saturation values from an external device via communication interface 290.

The components of oximetry device 200 that are shown and described as separate components are shown and described as such for illustrative purposes only. In some examples the functionality of some of the components may be combined in a single component. For example, the functionality of front end processing circuitry 216 and back-end processing circuitry 214 may be combined in a single processor system. Additionally, in some examples the functionality of some of the components of oximetry device 200 shown and described herein may be divided over multiple components. For example, some or all of the functionality of control circuitry 245 may be performed in front end processing circuitry 216, in back-end processing circuitry 214, or both. In other examples, the functionality of one or more of the components may be performed in a different order or may not be required. In some examples, all of the components of oximetry device 200 can be realized in processor circuitry.

In the above examples, processing circuitry 210, light drive circuitry 240, front end processing circuitry 216, and voltage measuring circuitry are described as performing the example techniques, wherein light drive circuitry 240, front end processing circuitry 216, and voltage measuring circuitry may be part of processing circuitry 210). However, any one or combination of processing circuitry 210, light drive circuitry 240, front end processing circuitry 216, and voltage measuring circuitry may be configured to perform the example techniques. For instance, the example techniques may be performed by circuitry, and an example of the circuitry includes any one or any combination of processing circuitry 210, light drive circuitry 240, front end processing circuitry 216, and voltage measuring circuitry.

Figure 4:
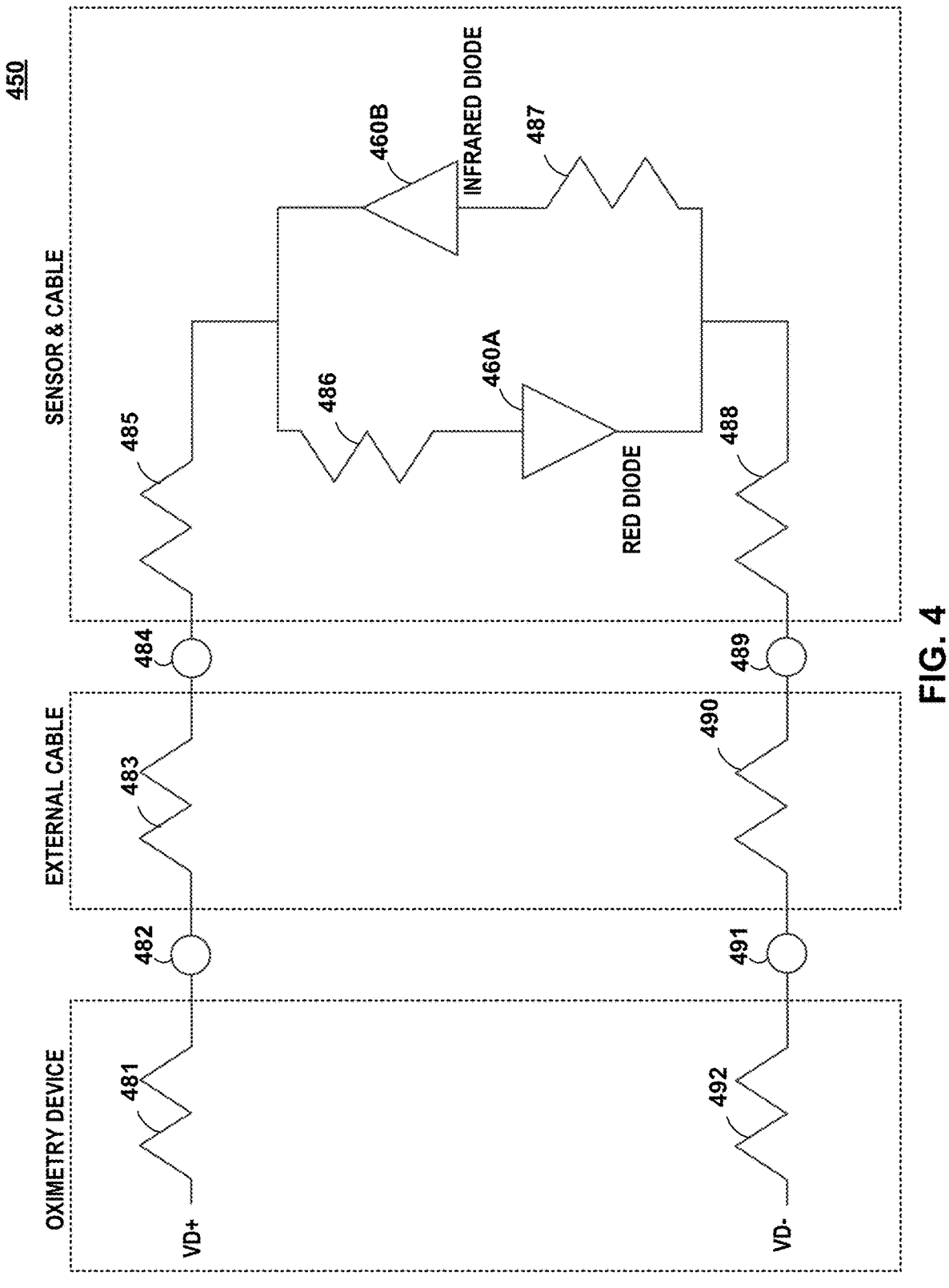
FIG. 4 is a conceptual diagram illustrating an example resistance schematic for light emitting diodes of a sensor device, in accordance with techniques described herein.
Figure 5B:
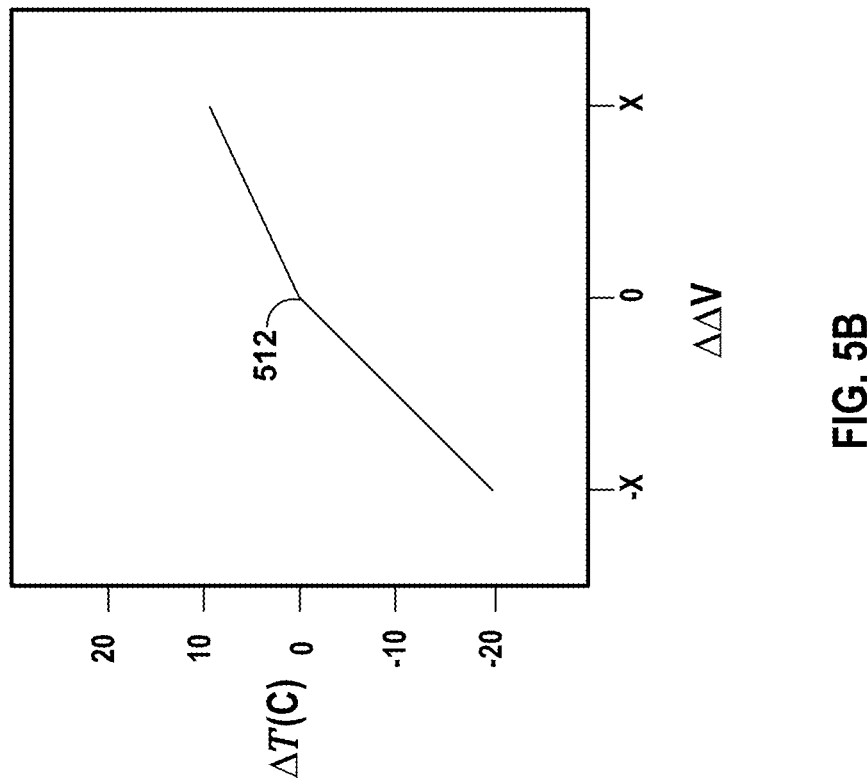
FIG. 5B is a conceptual diagram illustrating an example of a piecewise linear slope factor, in accordance with tech-niques described herein.
Figure 5A:
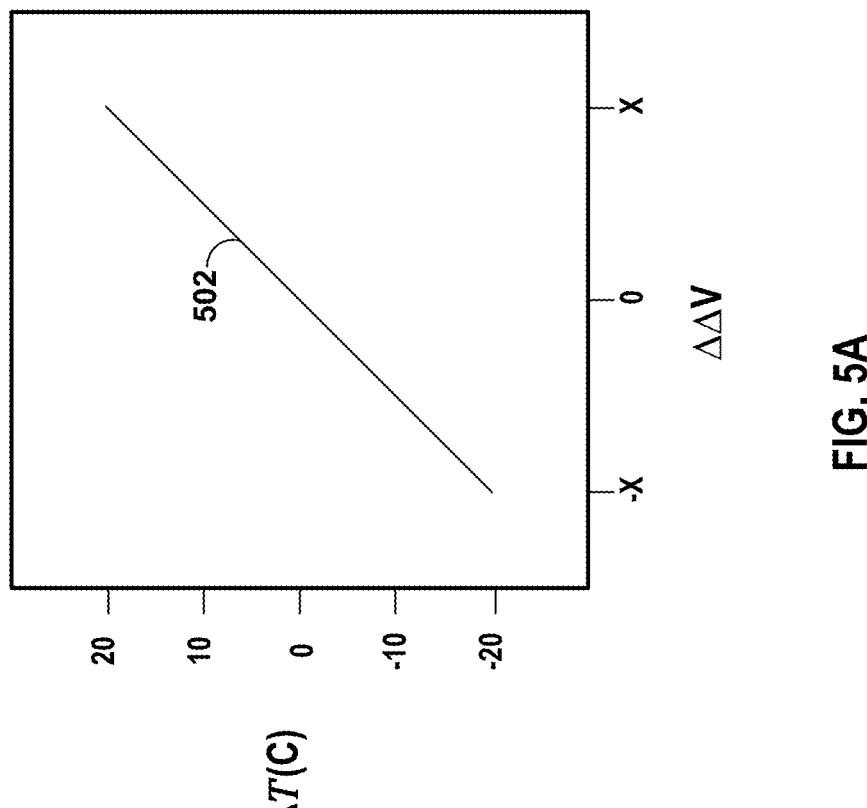
FIG. 5A is a conceptual diagram illustrating an example of a linear slope factor, in accordance with techniques described herein.

FIG. 3 illustrates an example graphical user interface 300 including autoregulation information presented on a display. FIG. 3 is an example of a presentation by processing circuitry 110 on display 132 shown in FIG. 1 or by processing circuitry 210 on display 232 shown in FIG. 2. Although FIGS. 3-5 are described with respect to processing circuitry 110 of oximetry device 100 (FIG. 1), in other examples, processing circuitry 210, 214, and/or 216 (FIG. 2), alone or in combination with processing circuitry 110, may perform any part of the techniques of FIGS. 3, 4, 5A, 5B, 6-8.

Graphical user interface 300 may be configured to display various information related to blood pressure, oxygen saturation, the COx index, limits of cerebral autoregulation, and/or cerebral autoregulation status. As shown, graphical user interface 300 may include oxygen saturation signal indicator 310, blood pressure signal indicator 320, and COx signal indicator 330. Graphical user interface 300 may include COx value indicator 340, autoregulation status indicator 350, and limit of autoregulation indicators 360 and 370.

Blood pressure signal indicator 320 may present a set of MAP values determined by processing circuitry 110 of oximetry device 100. The MAP values may be based on measured blood pressure values, but the raw measured blood pressure values (e.g., showing intra-cardia cycle variations) may be displayed in other examples. In some examples, blood pressure signal indicator 320 may present MAP values as discrete points over time or in a table. Blood pressure signal indicator 320 may also present MAP values as a moving average or waveform of discrete points. Blood pressure signal indicator 320 may present MAP values as a single value (e.g., a number) representing a current MAP value. Oxygen saturation signal indicator 310 and COx signal indicator 330 may also present rSO2 values and COx values, respectively, as discrete points, in a table, as a moving average, as a waveform, and/or as a single value. In other examples, the data from two or more of oxygen saturation signal indicator 310, blood pressure signal indicator 320, or COx signal indicator 330 may be combined together on a single graph.

COx signal indicator 330 may present a set of correlation coefficients determined by processing circuitry 110. Processing circuitry 110 may determine the correlation coefficients as a function of the oxygen saturation values presented in oxygen saturation signal indicator 310 and the MAP values presented in blood pressure signal indicator 320. In some examples, a COx value at or near one indicates the cerebral autoregulation status of a patient is impaired, as shown in autoregulation status indicator 350.

COx value indicator 340 shows a COx value determined by processing circuitry 110, which is shown as 0.8 in the example of FIG. 3 and may change over time. The COx value of 0.8 may result in a determination by processing circuitry 110 that the cerebral autoregulation status of the patient is impaired. Processing circuitry 110 may be configured to present, as the COx value in COx value indicator 340, the most recently determined COx value. In order to determine the cerebral autoregulation status of a patient for presentation in autoregulation status indicator 350, processing circuitry 110 may determine whether the most recent MAP value shown in blood pressure signal indicator 320 is between the limits of cerebral autoregulation presented in limit of autoregulation indicators 360 and 370. Processing circuitry 110 can present text such as "intact" or "impaired" in autoregulation status indicator 350. Processing circuitry 110 can also present a color such as green (e.g., for intact cerebral autoregulation) or red (e.g., for impaired cerebral autoregulation) to help aid a user's understanding of an autoregulation status of the patient.

In some examples, processing circuitry 110 may present limit of autoregulation indicators 360 and/or 370 in terms of blood pressure, for example, millimeters of mercury (mmHg). Processing circuitry 110 can determine the limits of cerebral autoregulation (LLA and ULA) for presentation in indicators 360 and 370 based on a relationship between the blood pressure of a patient and another physiological parameter of the patient. For example, indicator 360 may be highlighted when the LLA has been exceeded or indicator 360 may be highlighted when the ULA has been exceeded. In other examples, a single indicator may present the type of limit that has been exceed by the MAP value. If the LLA or ULA change, processing circuitry 110 may control user interface 300 to change the value of the LLA or ULA in accordance with any change to that respective value.

In some examples, processing circuitry 110 determines the cerebral autoregulation status for presentation in autoregulation status indicator 350 by comparing the most recently determined MAP value to the limits of cerebral autoregulation. For example, if processing circuitry 110 estimates the LLA at 50 mmHg and determines a MAP value at 40 mmHg, then processing circuitry 110 may determine that the cerebral autoregulation status of the patient is impaired, or not intact. In response to determining that the MAP value is less than or equal to the estimate of the LLA for more than the predetermined period of time, processing circuitry 110 may output a notification in autoregulation status indicator 350 as text, color, blinking, and/or any other suitable visible or audible manner.

FIG. 4 illustrates an example of a sensor device 450, in accordance with techniques described herein. The sensor device 450 may be an example of sensor device 150 of FIG. 1 and/or sensing device 250 of FIG. 2. Light emitting diode 460A and light emitting diode 460B (collectively, "light emitting diodes") may form an example of light source 260. Although FIG. 4 is described with respect to oximetry device 100 (FIG. 1), in other examples, other devices may perform any part of the technique of FIG. 4. For example, processing circuitry 210, 214, and/or 216 (FIG. 2), alone or in combination with processing circuitry 110, may perform any part of the technique of FIG. 4. In some examples, light emitting diodes 460 may include laser diodes, vertical-cavity surface-emitting lasers, or another device that emits light. In some examples, light emitting diodes 460 may additionally, or alternatively, include photodiodes or another device that detects light (e.g., red light, infrared light, etc.).

In the example of FIG. 4, light emitting diode 460A may be configured to emit red light, and light emitting diode 460B may be configured to emit infrared light. In some examples, however, light emitting diode 460A may be configured to emit infrared light and light emitting diode 460B may be configured to emit red light. Moreover, light emitting diodes 460 may be configured to emit light at wavelengths other than red and infrared. In the example of FIG. 4, light emitting diodes 460 are arranged in an anti-parallel configuration. For instance, the anode of light emitting diode 460B may be coupled to the cathode of light emitting diode 460A and the cathode of light emitting diode 460B may be coupled to the anode of light emitting diode 460A.

Each one of light emitting diodes 460 may have a respective body resistance. For example, light emitting diode 460A may include body resistance 486. Light emitting diode 460B may include body resistance 487. Body resistance 486 may correspond to (e.g., be equal to) body resistance 487. In some examples, body resistance 486 may be different from body resistance 487.

Processing circuitry 110 may apply a first current from a first terminal (e.g., VD+) through a first cable (e.g., an external cable and a cable, a cable only, etc.) to an anode of light emitting diode 460A and from a cathode of light emitting diode 460A through a second cable (e.g., an external cable and a cable, a cable only, etc.) to a second terminal (e.g., VD−). In this example, processing circuitry 110 may be configured to measure voltage across the first terminal (e.g., VD+) and the second terminal (e.g., VD−) while applying the first current. Similarly, processing circuitry 110 may apply a second current from the first terminal (e.g., VD+) through the first cable to the 460A anode and from the

460A cathode through the second cable to the second terminal (e.g., VD−). In this example, processing circuitry 110 may be configured to measure voltage across the first terminal (e.g., VD+) and the second terminal (e.g., VD−) while applying the second current.

FIG. 4 illustrates various examples of resistance that an oximeter may account for using techniques described herein. For example, a series resistance for connecting light emitting diode 460A to terminals VD+ and VD− of an oximeter (e.g., oximetry device 100, oximetry device 200, etc.) may include trace resistance 481, external cable resistance 483 (e.g., a DOC-10 CABLE), cable resistance 485, body resistance 486, cable resistance 488, external cable resistance 490, and trace resistance 492. Additionally, each one of connectors 482, 484, 489, and 491 may include a respective resistance. Similarly, a series resistance for connecting light emitting diode 460B to terminals VD+ and VD− of an oximeter (e.g., oximetry device 100, oximetry device 200, etc.) may include trace resistance 492, external cable resistance 490 (e.g., a DOC-10 CABLE), cable resistance 488, body resistance 487, cable resistance 485, external cable resistance 483, and trace resistance 481 (and additionally, each one of connectors 491, 489, 484, and 482 may include a respective resistance). While the example of FIG. 4 includes 2 light emitting diodes, examples may include more than 2 diodes (e.g., 4 diodes, 6 diodes, 8 diodes, 10 diodes, etc.).

Series resistance for connecting light emitting diodes 460 between terminals VD+ and VD−, which may represent an ohmic resistance between sensor device 450 and a device (e.g., oximetry device 100, oximetry device 200, etc.) can have several ohms of resistance which can bias the diode voltage reading of light emitting diodes 460. For example, an equivalent circuit may represent light emitting diode 460A with a series resistance that includes a summation of trace resistance 481, external cable resistance 483 (e.g., a DOC-10 CABLE), cable resistance 485, body resistance 486, cable resistance 488, external cable resistance 490, and trace resistance 492. Similarly, an equivalent circuit may represent light emitting diode 460B with a series resistance that includes trace resistance 492, external cable resistance 490 (e.g., a DOC-10 CABLE), cable resistance 488, body resistance 487, cable resistance 485, external cable resistance 483, and trace resistance 481. An oximetry device may be configured to increase accuracy of the measurement by using a very small current to help to reduce the voltage error generated from the series cable resistance.

In accordance with the techniques of the disclosure, a device (e.g., oximetry device 100, oximetry device 200, etc.) may be configured to determine a difference in voltage value for a light emitting diode based on a first voltage at the light emitting diode for a first current and a second voltage at the light emitting diode for a second current. For example, the device may calculate the difference in voltage value for the light emitting diode using EQUATION 1.

$$\Delta V = V(T, I1) - \frac{I1}{I2} V(T, I2) \qquad \text{EQUATION 1}$$

where V(T, I1) is a first voltage for a temperature 'T' at a first current (I1), V(T, I2) is a second voltage for a temperature 'T' at a second current (I2), and ΔV is a difference in voltage value for a light emitting diode. For instance, the device may multiply the second voltage (V(T, I2)) by a result of dividing the first current (I1) by the second current (I2) to generate a modified second voltage $$\left(\frac{I1}{I2}V(T, I2)\right)$$

and subtract the modified second voltage from the first voltage (V(T, I1)) to determine the difference in voltage value for the light emitting diode ($\Delta$V), which may refer to a field difference in voltage value light emitting diode ($\Delta V_F$) when the first voltage and the second voltage are measured in the "field" or a calibrated difference in voltage value light emitting diode ($\Delta V_M$) when the first voltage and the second voltage are measured at "manufacturing."

For example, a device (e.g., oximetry device 100, oximetry device 200, etc.) may measure a first voltage V(T, I1) at a light emitting diode 460A. In this example, the device may measure a second voltage V(T, I2) at light emitting diode 460A. In this example, the device can determine the difference in voltage value for light emitting diode 460A. For instance, the device may calculate EQUATION 1. Using a difference in voltage value for the light emitting diode may reduce or eliminate the effects of resistances 481-492, which may reduce or eliminate other measurement errors and might improve the temperature accuracy of the device in determining the sensitivity of the light emitting diode to temperature. Improving the temperature accuracy of the diode may improve the wavelength estimation of the diode, and this may improve an accuracy of the device in determining an oxygen saturation level.

The device (e.g., oximetry device 100, oximetry device 200, etc.) may determine a temperature for the light emitting diode based on the difference in voltage value using equation 1 and equation 2. For example, the device may calculate EQUATION 2.

$$T_F = T_M + \frac{\Delta T}{\Delta\Delta V}(\Delta V_F - \Delta V_M) \qquad \text{EQUATION 2}$$

where $T_F$ is a temperature of the light emitting diode in the field (e.g., a field temperature), $T_M$ is a temperature of the light emitting diode at manufacturing (e.g., a calibration temperature), $$\frac{\Delta T}{\Delta\Delta V}$$

is a slope factor (e.g., a change in temperature over a difference in a difference in voltage value for the light emitting diode), $\Delta V_F$ is a difference in voltage value for a light emitting diode in the field (e.g., a difference in voltage value), and $\Delta V_M$ is a difference in voltage value for the light emitting diode at manufacturing (e.g., a calibration difference in voltage value for the light emitting diode).

For example, a device (e.g., oximetry device 100, oximetry device 200, etc.) may determine (e.g., access, retrieve, etc.) the calibration temperature for light emitting diode 460A, the slope factor for light emitting diode 460A, and the calibration difference in voltage value for light emitting diode 460A from a storage device (e.g., memory 120) of the device. For example, during a calibration of light emitting diode 460A, the device may receive (e.g., be pre-programmed) with an indication of the calibration temperature for light emitting diode 460A, the slope factor for light emitting diode 460A, and the calibration difference in voltage value for light emitting diode 460A. In some examples, the slope factor for light emitting diode 460A may be for a set of light emitting diodes that includes light emitting diode 460A. For instance, the slope factor may be for a model and/or type of light emitting diode that includes light emitting diode 460A. Details on the slope factor are discussed with respect to FIGS. 5A, 5B.

A device (e.g., oximetry device 100, oximetry device 200, etc.) may calculate the temperate of light emitting diode 460A using EQUATION 2 with the retrieved calibration information (e.g., calibration temperature for light emitting diode 460A, the slope factor for light emitting diode 460A, and the calibration difference in voltage value for light emitting diode 460A) and the difference in voltage value for light emitting diode 460A determined using EQUATION 1.

Similarly, a device (e.g., oximetry device 100, oximetry device 200, etc.) may calculate the temperate of light emitting diode 460B using EQUATION 2 with the retrieved calibration information (e.g., calibration temperature for light emitting diode 460B, the slope factor for light emitting diode 460B, and the calibration difference in voltage value for light emitting diode 460B) and the difference in voltage value for light emitting diode 460B determined using EQUATION 1.

For example, a device (e.g., oximetry device 100, oximetry device 200, etc.) may determine a slope factor, a calibration temperature of the light emitting diode during a calibration process for the light emitting diode, and a calibration difference in voltage value for the light emitting diode measured during the calibration process. In this example, the device may subtract the calibration difference in voltage value for light emitting diode 460B from the difference in voltage value for light emitting diode 460B. The device may multiply the slope factor to a result of the subtraction to generate a temperature difference value. In this example, the device may add the calibration temperature to the temperature difference value.

A device (e.g., oximetry device 100, oximetry device 200, etc.) may validate the light emitting diodes 460 using the temperature at light emitting diode 460A and the temperature at light emitting diode 460B. For example, the device may determine that light emitting diodes 460 are valid when a difference between the temperature at light emitting diode 460A (e.g., as calculated using EQUATIONS 1 and 2) and the temperature at light emitting diode 460B (e.g., as calculated using EQUATIONS 1 and 2) is less than a threshold value. The threshold value may be preconfigured. In some examples, the threshold value is configurable.

A device (e.g., oximetry device 100, oximetry device 200, etc.) may be configured to use the temperature to correct for any shifts in wavelength, especially for red light. For an operating temperature range of 0° C. to 40° C., a wavelength of red light could shift several nm, which may result in SpO2 errors. For example, the device may be configured to calculate EQUATION 3.

$$\lambda_c = \lambda_m + (\lambda_{Coeff}*(T_F - T_m)) \qquad \text{EQUATION 3}$$

where $\lambda_c$ is the calculated/estimated wavelength, $\lambda_m$ is the wavelength measured at manufacturing, $\lambda_{Coeff}$ is the temperature coefficient of the diode (e.g., an average characterization for each type of LED used), $T_F$ is the field temperature of the diode as measured by the oximeter in the field, and $T_m$ is the temperature of the diode at manufacturing when the wavelength was measured. The slope term $\lambda_{Coeff}$ and the temperature of the diode at manufacturing when the wavelength was measured $T_m$ could be stored on the memory of the sensor.

A device (e.g., oximetry device 100, oximetry device 200, etc.) may be configured to apply Sp02 compensation. For example, the device may apply corrections for SpO2 errors in extreme temperatures based on compensated wavelength. This may be helpful for emergency medical services (EMS) which often work in outdoor environments. For example, an outdoor environment may be excessively hot or cold, which can lead to SpO2 errors. With this compensation, the device may mitigate or remove error from environments that deviate from a nominal temperature or temperature range. The device may be configured to compensate using the wavelength change or just a calibration adjustment.

FIG. 5A is a conceptual diagram illustrating an example of a linear slope factor, in accordance with techniques described herein. The abscissa axis of FIG. 5A represents a difference in a difference in voltage value for a light emitting diode ($\Delta\Delta V$), and the ordinate axis of FIG. 5A represents a change in temperature in Celsius (° C.). The example of FIG. 5A is discussed with reference to FIGS. 1-4 for example purposes only.

In the example of FIG. 5A, a linear curve 502 is fit to samples of a measured difference in a difference in voltage value for a light emitting diode for different changes in temperature. A device (e.g., oximetry device 100, oximetry device 200, etc.) may use a slope of linear curve 502 as the slope factor $$\left(\frac{\Delta T}{\Delta\Delta V}\right),$$

for example, when using EQUATION 2.

FIG. 5B is a conceptual diagram illustrating an example of a piecewise linear slope factor, in accordance with techniques described herein. The abscissa axis of FIG. 5B represents a difference in a difference in voltage value for a light emitting diode ($\Delta\Delta V$), and the ordinate axis of FIG. 5B represents a change in temperature in Celsius (° C.). The example of FIG. 5B is discussed with reference to FIGS. 1-4 for example purposes only.

In the example of FIG. 5B, a piece-wise linear curve 512 is fit to samples of a measured difference in a difference in voltage value for a light emitting diode for different changes in temperature. A device (e.g., oximetry device 100, oximetry device 200, etc.) may use a first (left-most) slope of linear curve 502 as the slope factor $$\left(\frac{\Delta T}{\Delta\Delta V}\right)$$

when $\Delta V_F$ minus $\Delta V_M$ is less than 0 and a second (right-most) slope of linear curve 502 as the slope factor $$\left(\frac{\Delta T}{\Delta\Delta V}\right)$$

when $\Delta V_F$ minus $\Delta V_M$ is greater than 0. While this example has two linear pieces, other examples may comprise more than two linear pieces. Moreover, while the example of FIG. 5B has a position that separates a first linear piece and a second linear piece at a difference in a difference in voltage value for a light emitting diode ($\Delta\Delta V$) of 0, in other examples, the position that separates two different linear pieces may be different (e.g., greater than 0 or less than 0). Further, in some examples, other curve fitting techniques may be used to generate the slope factor $$\left(\frac{\Delta T}{\Delta\Delta V}\right)$$

from samples. For example, a polynomial function may be used to generate the slope factor, with one or more added terms to account for the higher order variables. For example, if a 2nd order polynomial was used, the device may use an additional coefficient for the squared term.

A device (e.g., oximetry device 100, oximetry device 200, etc.) may be configured to extract an absolute temperature estimation from each LED in sensing device(s) 150. Techniques described herein for performing absolute temperature estimation may test the LED at specific currents (e.g., I1 and I2 of Equation 1), which may result in a momentary pause in taking optical measurements like pulse oximetry measurements. when updating the temperature measurement using the process to extract an absolute temperature, the device may pause pulse oximetry measurement and remeasure the LEDs at the specified currents.

In some examples, a device (e.g., oximetry device 100, oximetry device 200, etc.) may be configured to calculate a relative change in temperature using any current. In this way, the device may determine an updated temperature while continuing to provide pulse oximetry measurements. For example, the device may determine a change in voltage over time of each LED (e.g., a difference in voltage). In this example, the device may use a previously characterized temperature coefficient, referred to herein as "dV/dT" that may be stored in the device (e.g., in EPROM and/or Digical).

For example, a device (e.g., oximetry device 100, oximetry device 200, etc.) may be configured to determine an absolute temperature when sensing device(s) 150 are connected to the device. For example, the device may determine the absolute temperature using equations 1 and 2. The device may track the temperature change relative to the initial temperature using the temperature coefficient (dV/dT). The device may continuously measure the forward voltage (VF) of each LED of sensing device(s) 150 and calculate a differential voltage (dV). In this example, the device may divide the differential voltage by a temperature coefficient (dT/dV) to get a differential temperature (dT). In this example, the device may add the differential temperature to the original estimated temperature (e.g., the absolute temperature determined using equations 1 and 2) to get an absolute temperature (T). In this way, the device can determine a temperature trend for each LED of sensing device(s) 150, while the device is performing oximetry measurements.

In some examples, a device (e.g., oximetry device 100, oximetry device 200, etc.) may be configured to improve an accuracy of the determined absolute temperature based on a change in current. For example, the device may "zero" the differential voltage (dV) when LED current changes. For instance, the device may set a non-zero differential voltage (dV) to zero when a change in current flowing through the LED exceeds a current threshold value. In this way, the device may help to remove changes in the differential voltage that are due to changes in LED current for a buffered period around when the LED current changes. It may be desirable to remove such changes in the differential voltage because the change in the differential voltage may be caused by current change and not temperature.

In some examples, a device (e.g., oximetry device 100, oximetry device 200, etc.) may be configured to improve an accuracy of the determined absolute temperature based on an elapsed time since determining the absolute temperature using a temperature coefficient. For example, the device may determine to trend the temperature for a maximum period of time and/or for a maximum temperature change. In some examples, in response to a device (e.g., oximetry device 100, oximetry device 200, etc.) determining that the absolute temperature determined using a temperature coefficient goes beyond a temperature threshold (e.g., exceeds the temperature threshold), the device may recalculate the absolute temperature (e.g., using Equations 1 and 2) and restart temperature trending (e.g., determine the absolute temperature using a temperature coefficient and the recalculated absolute temperature.

In some examples, the device may trigger a remeasurement of absolute temperature if the two LEDs start to accumulate a large disagreement with each other. For example, the device may determine a first absolute temperature determined using a red LED of sensing device(s) 150 and determine a second absolute temperature determined using an infrared LED of sensing device(s) 150. In this example, the device may determine to trigger a remeasurement of absolute temperature (e.g., using Equations 1 and 2) when a difference between the first absolute temperature and the second absolute temperature exceeds a temperature difference threshold. In this way, the device may help to improve an accuracy of the temperature measurement when LEDs of sensing device(s) 150 should read as approximately the same temperature. For instance, LEDs of sensing device(s) 150 should read as approximately the same temperature when LEDs of sensing device(s) 150 are positioned near each other in a same physical package. In some examples, the device may periodically (e.g., every 5 minutes, 30 mins, etc.) recalculate the absolute temperature and restart temperature trending to help too remove accumulated error.

In some examples, a device (e.g., oximetry device 100, oximetry device 200, etc.) may be configured to calculate a change in temperature using EQUATION 3 (e.g., a $\Delta V$ $\Delta T$: Method 0).

$$\frac{\Delta V_{(0)}}{\Delta T} = \frac{V(T1,I) - V(T2,I)}{T1 - T2} \qquad \text{EQUATION 3}$$

where $\Delta T$ is the difference in temperature, $\Delta V_{(0)}$ is a difference in voltage, I is a current at the diode (e.g., an LED of sensing device(s) 150), T1 is a first temperature, T2 is a second temperature, V(T1, I) is a forward voltage at the diode at the first temperature (T1) and at the current (I), V(T2, I) is a forward voltage at the diode at the second temperature (T2).

In this way, the device may calculate the change in temperature ($\Delta T$) used on a single LED, used with matching current (I) while resistance is fixed (e.g., from manufacturing phase to field and/or measurement phase).

In some examples, a device (e.g., oximetry device 100, oximetry device 200, etc.) may be configured to calculate a temperature using EQUATIONS 1 and 2 (e.g., Ideality Factor method: Method 1).

In some examples, a device (e.g., oximetry device 100, oximetry device 200, etc.) may be configured to calculate a temperature using EQUATION 4 (e.g., $\Delta V$ $\Delta T$: Method 2)

$$\frac{\Delta \Delta V_{(2)}}{\Delta T} = \frac{\Delta V(T1,I) - \Delta V(T2,I)}{T1 - T2}, \Delta V = V_{Red}(T,I) - V_{IR}(T,I) \qquad \text{EQUATION 4}$$

where $\Delta T$ is the difference in temperature, $\Delta VV_{(2)}$ is a difference in difference in voltage, I is a current at the diode (e.g., an LED of sensing device(s) 150), T1 is a first temperature, T2 is a second temperature, V (T1, I) is a forward voltage at the diode at the first temperature (T1) and at the current (I), V(T2, I) is a forward voltage at the diode at the second temperature (T2), $V_{Red}$(T, I) is a forward voltage at a red diode at the temperature (T) and at the current (I) and $V_{IR}$(T, I) is a forward voltage at an infrared diode at the temperature (T) and at the current (I).

In this way, the device may calculate the change in temperature ($\Delta T$) using the difference between red LED and infrared LEDs first, using a matching current (I), and resistance can vary (e.g., from manufacturing phase to field and/or measurement phase).

In some examples, a device (e.g., oximetry device 100, oximetry device 200, etc.) may be configured to calculate a temperature using EQUATION 5 (e.g., $\Delta V$ $\Delta T$: Method 3).

$$\frac{\Delta \Delta V_{(3)}}{\Delta T} = \frac{\Delta V(T1,I) - \Delta V(T2,I)}{T1 - T2}, \qquad \text{EQUATION 5}$$

$$\Delta V = V(T,I1) - \frac{I1}{I2} V(T,I2)$$

where $\Delta T$ is the difference in temperature, $\Delta VV_{(3)}$ is a difference in difference in voltage, I is a current at the diode (e.g., an LED of sensing device(s) 150), T1 is a first temperature, T2 is a second temperature, V (T1, I) is a forward voltage at the diode at the first temperature (T1) and at the current (I), V(T2, 1) is a forward voltage at the diode at the second temperature (T2), I1 is a current at a diode (e.g., an LED of sensing device(s) 150) and I2 is a second current at the diode.

In this way, the device may calculate the change in temperature ($\Delta T$) using a single LED and resistance can vary (e.g., from manufacturing phase to field and/or measurement phase).

A device (e.g., oximetry device 100, oximetry device 200, etc.) may be configured to may calculate EQUATION 6.

$$T_F = T_M + \frac{\Delta T}{\Delta V}(V_F - V_M) \qquad \text{EQUATION 6}$$

where $T_F$ is a temperature of the light emitting diode in the field (e.g., a field temperature), $T_M$ is a temperature of the light emitting diode at manufacturing (e.g., a calibration temperature), $$\frac{\Delta T}{\Delta V}$$

is an inverted $\Delta V/\Delta T$ for a LED based on population characterization, $V_F$ is a voltage value for a light emitting diode in the field, and $V_M$ is a voltage value for the light emitting diode at manufacturing (e.g., a calibration difference in voltage value for the light emitting diode).

TABLE 1

AV AT Methods comparison

| Process | Independent Temperature measurements | Cancels Cable resistance | Cancels LED body resistance | Signal level | Conclusion |
|---|---|---|---|---|---|
| ΔV ΔT Method 0 | Yes | Only if fixed | Only if fixed | | Cannot use for standard applications. Because R varies between manufacturer and field. |
| Method 1 | | | | | N.A. |
| ΔV ΔT Method 2 | No | Yes | No/partially | good | Good |
| ΔV ΔT Method 3 | Yes | Yes | Yes | good | Good |
| ΔV ΔT Method 4 | Yes | Yes | Yes | low | Do not use, signal level too low. |

Figure 6:
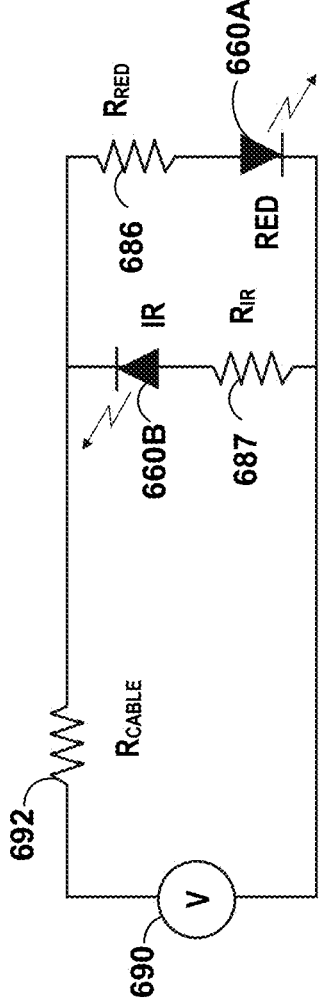
FIG. 6 is a conceptual diagram illustrating an example resistance schematic for light emitting diodes of a sensor device for determining a difference in temperature, in accor-dance with techniques described herein.

FIG. 6 is a conceptual diagram illustrating an example resistance schematic for light emitting diodes of a sensor device for determining a difference in temperature, in accordance with techniques described herein. The example of FIG. 6 includes a voltage source 690, a resistance 692 (e.g., one or more of resistances 481-492), red light emitting diode 660A, which includes body resistance 687, and infrared light emitting diode 660B, which includes body resistance 686.

A device (e.g., oximetry device 100, oximetry device 200, etc.) may be configured to calculate an absolute voltage measurement confounded through uncertainty in the contact resistances of the devices using EQUATIONS 7 and 8.

$$V = nV_T \ln\frac{I}{I_S} + I(R_{Cable} + R_{LED}) \qquad \text{EQUATION 7}$$

$$V_T = \frac{K_B T}{q} \qquad \text{EQUATION 8}$$

where V is a voltage at voltage source 690, n is the ideality constant, T is a temperature at the diode (e.g., light emitting diode 660A or light emitting diode 660B) in Kelvins, $K_B$ is the Boltzmann's constant, q is the charge of an electron, I is current at the diode, $R_{Cable}$ is a resistance at resistance 692, and $R_{LED}$ is a body resistance of the diode (e.g., body resistance 686 or body resistance 687.

If the cable does not change, e.g., the cable has not been swapped between two temperatures, and the device is in a single oximetry session, EQUATION 9 (e.g., Method 0) may translate to EQUATION 10 (ignoring some temperate dependent resistance change and assuming that current is not changing).

$$\frac{dV}{dT} = \frac{d}{dT}\left(nV_T \ln\frac{I}{I_S}\right) + \frac{d}{dT}(I(R_{Cable} + R_{LED})) \qquad \text{EQUATION 9}$$

$$\frac{dV}{dT} = \frac{d}{dT}\left(nV_T \ln\frac{I}{I_S}\right) \qquad \text{EQUATION 10}$$

EQUATION 10 may result in the temperature dependence of the diode itself.

Figure 7:
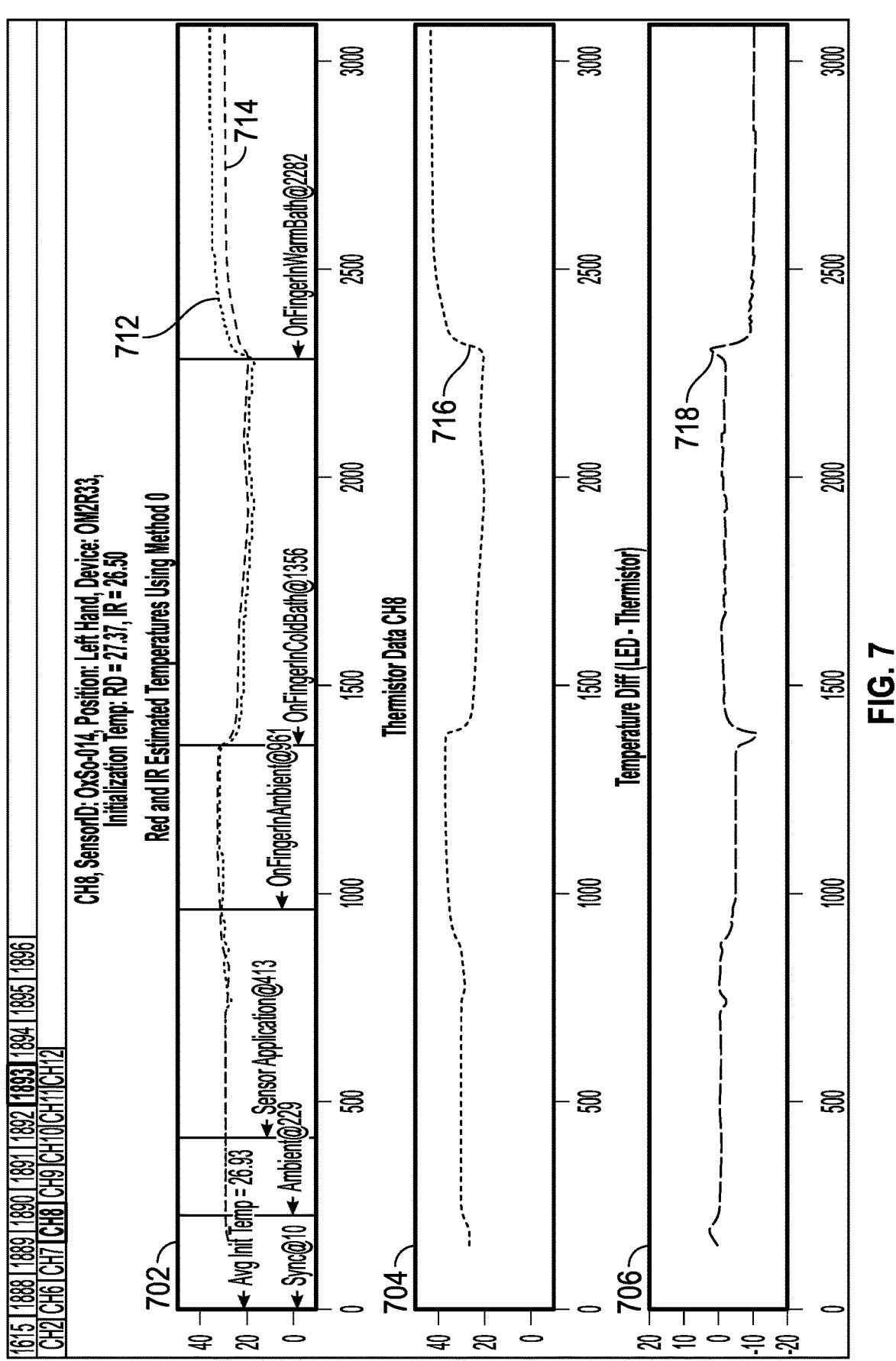
FIG. 7 is a conceptual diagram illustrating an example of estimating the temperature while running pulse oximetry, in accordance with techniques described herein.

FIG. 7 is a conceptual diagram illustrating an example of estimating the temperature while the system is running pulse oximetry, in accordance with techniques described herein. FIG. 7 illustrates a red and infrared diode estimated temperature 702, thermistor data 704, and a temperature difference 706. Specifically, red and infrared diode estimated temperature 702 illustrates a first diode temperature 712 and a second diode temperature 714. Thermistor data 704 illustrates a measured temperature value 716. Temperature difference 706 illustrates a difference between the estimated diode temperature shown in red and infrared diode estimated temperature 702 and the measured temperature value 716 shown in thermistor data 704.

In the example of FIG. 7, a device (e.g., oximetry device 100, oximetry device 200, etc.) may be configured to determine the average of the two initialization temperatures to get an absolute estimate of the initial temperature using EQUATIONS 1 and 2. In this example, the device may estimate the temperature while the system is normally running pulse oximetry (e.g., using EQUATION 3). As shown in FIG. 7, the Red and IR estimates of first diode temperature 712 and a second diode temperature 714 track the temperature illustrated in thermistor data 704 well compared to an external temperature sensor (e.g., a thermistor).

FIG. 8 is a flow chart illustrating an example process of estimating temperature, in accordance with techniques described herein. A device (e.g., oximetry device 100, oximetry device 200, or more specifically, front end processing circuitry 216 and/or back end processing circuitry 214) may determine a difference in voltage value for a light emitting diode based on a first voltage at the light emitting diode for a first current and a second voltage at the light emitting diode for a second current, wherein the difference in voltage value is dependent on a temperature at the light emitting diode (802). For example, the device may multiply the second voltage by a result of dividing the first current by the second current to generate a modified second voltage and subtract the modified second voltage from the first voltage. In some examples, the device may determine the difference in voltage value using EQUATION 1. The light emitting diode may be configured to, for example, emit red light or emit infrared light.

The device may determine a temperature for the light emitting diode based on the difference in voltage value (804). For example, the device may determine the temperature for the light emitting diode based on the difference in voltage value and based further on configuration information. Calibration information may include, for example, one or more of a calibration temperature for a light emitting diode, a slope factor for the light emitting diode, or a calibration difference in voltage value for the light emitting diode during a calibration of the light emitting diode. For instance, during a calibration of a light emitting diode, the device may receive (e.g., be pre-programmed) with an indication of the calibration temperature for the light emitting diode, the slope factor for the light emitting diode, and the calibration difference in voltage value for the light emitting diode.

For example, the device may determine a slope factor, a calibration temperature of the light emitting diode during a calibration process for the light emitting diode, and a calibration difference in voltage value for the light emitting diode measured during the calibration process. In this example, the device may subtract the calibration difference in voltage value for the light emitting diode from the difference in voltage value for the light emitting diode, multiply the slope factor to a result of the subtraction to generate a temperature difference value, and add the calibration temperature to the temperature difference value. For instance, the device may determine the temperature using EQUATION 2.

In some examples, a device (e.g., oximetry device 100, oximetry device 200, or more specifically, front end processing circuitry 216 and/or back end processing circuitry 214) may determine a temperature at a second light emitting diode. For example, the device may determine a second difference in voltage value for a second light emitting diode based on a first voltage at the second light emitting diode for a first current at the second light emitting diode and a second voltage at the second light emitting diode for a second current at the second light emitting diode. In this example, the device may determine a temperature for the second light emitting diode based on the second difference in voltage value for the second light emitting diode, wherein the determination that the first light emitting diode is valid is further based on the temperature for the second light emitting diode.

The device may determine an intensity of a received photonic signal corresponding to an output photonic signal output using the light emitting diode (806). For example, the device may estimate a wavelength for the output photonic signal based on the temperature at the light emitting diode. In this example, the device may determine the oxygen saturation level based on the intensity of the received photonic signal and further based on the estimated wavelength for the output photonic signal.

The device may determine an oxygen saturation level based on the intensity of the received photonic signal and the temperature for the light emitting diode (808). For example, the device may drive the light emitting diode to output the output photonic signal towards a subject's tissue and receive, from a detector, the received photonic signal after the output photonic signal transmits through the subject's tissue. The device may output an indication of the oxygen saturation level (810). For example, the device may output the indication of the oxygen saturation level to another device and/or a display.

In some examples, a device (e.g., oximetry device 100, oximetry device 200, or more specifically, front end processing circuitry 216 and/or back end processing circuitry 214) may determine a second difference in voltage value for a light emitting diode based on a third voltage at the light emitting diode for a third current and the first voltage (812). For example, the device may measure the third voltage while the device drives the light emitting diode at the third current. In some examples, the device or another device may drive the light emitting diode at the third current for determining an oxygen saturation level.

The device may determine a difference in temperature value based on the second difference in voltage (814). For example, the device may multiply the second difference in voltage with a factor indicating a change in temperature over a change in voltage for the light emitting diode. For example, the factor may include an inverted ΔV/ΔT for a LED $$\left(\text{i.e., } \frac{\Delta T}{\Delta V}\right)$$

based on population characterization.

The device may determine an updated temperature for the light emitting diode based on the difference in temperature value and the temperature for the light emitting diode based on the difference in voltage value (816). For example, the device may add the difference in temperature value to the temperature value determined in step 814. In some examples, the device may the device may add the difference in temperature value to a temperature value determined, for example, using a previously updated temperature or using a measured temperature.

In some examples, a device (e.g., oximetry device 100, oximetry device 200, or more specifically, front end processing circuitry 216 and/or back end processing circuitry 214) may in response to a determination that a difference in current at the light emitting diode based on the first current and the third current is greater than a threshold current value, set the second difference in voltage value for the light emitting diode to zero. In this way, the device may zero-out temperature measurements that occur from a change in current.

In some examples, the device may periodically reset to a new temperature value. For example, the device may initiate a timer in response to the determination of the temperature for the light emitting diode. In this example, the device may, in response to a determination that the time has elapsed, determine the updated temperature for the light emitting diode based on EQUATIONS 1 and 2. For example, the device may determine the updated temperature for the light emitting diode based on a third difference in voltage value for the light emitting diode that is based on a fourth voltage at the light emitting diode for a fourth current and a fifth voltage at the light emitting diode for a fifth current, wherein the third difference in voltage value is dependent on the temperature at the light emitting diode.

The oximetry device may determine an updated oxygen saturation level based on the intensity of the received photonic signal and the updated temperature for the light emitting diode (818). For example, the device may drive the light emitting diode to output the output photonic signal towards a subject's tissue and receive, from a detector, the received photonic signal after the output photonic signal transmits through the subject's tissue. The oximetry device may output an indication of the updated oxygen saturation level (820). For example, the device may output the indication of the oxygen saturation level to another device and/or a display.

The following examples are a non-limiting list of examples in accordance with one or more techniques of this disclosure.

Clause 1. A device for measuring oxygen saturation, the device comprising circuitry configured to: determine a difference in voltage value for a light emitting diode based on a first voltage at the light emitting diode for a first current and a second voltage at the light emitting diode for a second current, wherein the difference in voltage value is dependent on a temperature at the light emitting diode; determine a temperature for the light emitting diode based on the difference in voltage value; determine an intensity of a received photonic signal corresponding to an output photonic signal output using the light emitting diode; determine an oxygen saturation level based on the intensity of the received photonic signal and the temperature for the light emitting diode; and output an indication of the oxygen saturation level.

Clause 2. The device of clause 1, wherein, to determine the difference in voltage value, the circuitry is configured to: multiply the second voltage by a result of dividing the first current by the second current to generate a modified second voltage; and subtract the modified second voltage from the first voltage.

Clause 3. The device of any of clauses 1-2, wherein, to determine the difference in voltage value, the circuitry is configured to calculate:

$$\Delta V = V(T,I1) - \frac{I1}{I2} V(T,I2)$$

where V(T, I1) is the first voltage for a temperature 'T' at the first current (I1), V(T, I2) is the second voltage for the temperature 'T' at the second current (I2), and $\Delta V$ is the difference in voltage value for the light emitting diode.

Clause 4. The device of any of clauses 1-3, wherein, to determine the temperature, the circuitry is configured to determine the temperature for the light emitting diode based on the difference in voltage value and based further on configuration information.

Clause 5. The device of any of clauses 1-4, wherein, to determine the temperature, the circuitry is configured to determine the temperature for the light emitting diode based on the difference in voltage value and based further on a calibration temperature of the light emitting diode during a calibration process for the light emitting diode.

Clause 6. The device of any of clauses 1-5, wherein, to determine the temperature, the circuitry is configured to determine the temperature for the light emitting diode based on the difference in voltage value and based further on a calibration difference in voltage value for the light emitting diode measured during a calibration process.

Clause 7. The device of any of clauses 1-6, wherein, to determine the temperature, the circuitry is configured to: determine a slope factor, a calibration temperature of the light emitting diode during a calibration process for the light emitting diode, and a calibration difference in voltage value for the light emitting diode measured during the calibration process; subtract the calibration difference in voltage value for the light emitting diode from the difference in voltage value for the light emitting diode; multiply the slope factor to a result of the subtraction to generate a temperature difference value; and add the calibration temperature to the temperature difference value.

Clause 8. The device of any of clauses 1-7, wherein, to determine the temperature, the circuitry is configured to calculate:

$$T_F = T_M + \frac{\Delta T}{\Delta \Delta V} (\Delta V_F - \Delta V_M)$$

where $T_F$ is the temperature of the light emitting diode, $T_M$ is a calibration temperature during a manufacturing calibration process, $$\frac{\Delta T}{\Delta \Delta V}$$

is a slope factor, a $\Delta_F$ is the difference in voltage value for the light emitting diode, and $\Delta V_M$ is a difference in voltage value for the light emitting diode during the manufacturing calibration process.

Clause 9. The device of any of clauses 1-8, wherein the circuitry is configured to determine whether the light emitting diode is valid to use for temperature estimation based on the temperature for the light emitting diode, wherein the determination of the intensity of the received photonic signal is in response to the determination that the light emitting diode is valid.

Clause 10. The device of clause 9, wherein the light emitting diode comprises a first light emitting diode and wherein the circuitry is further configured to: determine a second difference in voltage value for a second light emitting diode based on a first voltage at the second light emitting diode for a first current at the second light emitting diode and a second voltage at the second light emitting diode for a second current at the second light emitting diode; and determine a temperature for the second light emitting diode based on the second difference in voltage value for the second light emitting diode, wherein the determination that the first light emitting diode is valid is further based on the temperature for the second light emitting diode.

Clause 11. The device of any of clauses 1-10, wherein the circuitry is configured to estimate a wavelength for the output photonic signal based on the temperature at the light emitting diode, wherein to determine the oxygen saturation level, the circuitry is configured to determine the oxygen saturation level based on the intensity of the received photonic signal and further based on the estimated wavelength for the output photonic signal.

Clause 12. The device of any of clauses 1-11, wherein the circuitry is configured to: drive the light emitting diode to output the output photonic signal towards a subject's tissue; and receive, from a detector, the received photonic signal after the output photonic signal transmits through the subject's tissue.

Clause 13. The device of any of clauses 1-12, wherein the light emitting diode is configured to emit red light or emit infrared light.

Clause 14. The device of any of clauses 1-13, wherein the circuitry is configured to: determine a second difference in voltage value for the light emitting diode based on a third voltage at the light emitting diode for a third current and the first voltage; determine a difference in temperature value based on the second difference in voltage; and determine an updated temperature for the light emitting diode based on the difference in temperature value and the temperature for the light emitting diode based on the difference in voltage value.

Clause 15. The device of clause 14, wherein the circuitry is configured to: determine an updated oxygen saturation level based on the intensity of the received photonic signal and the updated temperature for the light emitting diode; and output an indication of the updated oxygen saturation level.

Clause 16. The device of any of clauses 14-15, wherein, to determine the difference in temperature value, the circuitry is configured to multiply the second difference in voltage with a factor indicating a change in temperature over a change in voltage for the light emitting diode.

Clause 17. The device of any of clauses 14-16, wherein, to determine the second difference in voltage value, the circuitry is configured to: in response to a determination that a difference in current at the light emitting diode based on the first current and the third current is greater than a threshold current value, set the second difference in voltage value for the light emitting diode to zero.

Clause 18. The device of any of clauses 14-17, wherein the circuitry is further configured to: initiate a timer in response to the determination of the temperature for the light emitting diode; and in response to determining that the time has elapsed, determine the updated temperature for the light emitting diode based on a third difference in voltage value for the light emitting diode that is based on a fourth voltage at the light emitting diode for a fourth current and a fifth voltage at the light emitting diode for a fifth current, wherein the third difference in voltage value is dependent on the temperature at the light emitting diode.

Clause 19. A method for measuring oxygen saturation, the method comprising: determining a difference in voltage value for a light emitting diode based on a first voltage at the light emitting diode for a first current and a second voltage at the light emitting diode for a second current; determining a temperature for the light emitting diode based on the difference in voltage value; determining an intensity of a received photonic signal corresponding to an output photonic signal output using the light emitting diode; determining an oxygen saturation level based on the intensity of the received photonic signal and the temperature for the light emitting diode; and outputting an indication of the oxygen saturation level.

Clause 20. A system for measuring oxygen saturation, the system comprising: a sensor device comprising a light emitting diode; and an oximetry device comprising circuitry configured to: determine a difference in voltage value for the light emitting diode based on a first voltage at the light emitting diode for a first current and a second voltage at the light emitting diode for a second current; determine a temperature for the light emitting diode based on the difference in voltage value; determine an intensity of a received photonic signal corresponding to an output photonic signal output using the light emitting diode; determine an oxygen saturation level based on the intensity of the received photonic signal and the temperature for the light emitting diode; and output an indication of the oxygen saturation level.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory. The computer-readable storage media may be referred to as non-transitory. A programmer, such as patient programmer or clinician programmer, or other computing device may also contain a more portable removable memory type to enable easy data transfer or offline data analysis.

The techniques described in this disclosure, including those attributed to devices 100 and 200, processing circuitry 110, 210, 214, and 216, memories 120 and 220, displays 132 and 232, sensing circuitries 140-142, circuitries 240 and 245, sensing devices 150, 151, 152, and 250, and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in patient monitors, such as multiparameter patient monitors (MPMs) or other devices, remote servers, or other devices. The term "processor" or "processing circuitry" may generally refer to any of the foregoing logic circuitry, alone or in combination with other logic circuitry, or any other equivalent circuitry.

As used herein, the term "circuitry" refers to an ASIC, an electronic circuit, a processor (shared, dedicated, or group) and memory that execute one or more software or firmware programs, a combinational logic circuit, or other suitable components that provide the described functionality. The term "processing circuitry" refers one or more processors distributed across one or more devices. For example, "processing circuitry" can include a single processor or multiple processors on a device. "Processing circuitry" can also include processors on multiple devices, wherein the operations described herein may be distributed across the processors and devices.

Such hardware, software, firmware may be implemented within the same device or within separate devices to support the various operations and functions described in this disclosure. For example, any of the techniques or processes described herein may be performed within one device or at least partially distributed amongst two or more devices, such as between devices 100 and 200, processing circuitry 110, 210, 214, and 216, memories 120 and 220, sensing circuitries 140-142, and/or circuitries 240 and 245. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in an article of manufacture including a non-transitory computer-readable storage medium encoded with instructions. Instructions embedded or encoded in an article of manufacture including a non-transitory computer-readable storage medium encoded, may cause one or more programmable processors, or other processors, to implement one or more of the techniques described herein, such as when instructions included or encoded in the non-transitory computer-readable storage medium are executed by the one or more processors. Example non-transitory computer-readable storage media may include RAM, ROM, programmable ROM (PROM), erasable programmable ROM (EPROM), electronically erasable programmable ROM (EEPROM), flash memory, a hard disk, a compact disc ROM (CD-ROM), a floppy disk, a cassette, magnetic media, optical media, or any other computer readable storage devices or tangible computer readable media.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache). Elements of devices and circuitry described herein, including, but not limited to, devices 100 and 200, processing circuitry 110, 210, 214, and 216, memories 120 and 220, displays 132 and 232, sensing circuitries 140-142, circuitries 240 and 245, sensing devices 150-152 and 250 may be programmed with various forms of software. The one or more processors may be implemented at least in part as, or include, one or more executable applications, application modules, libraries, classes, methods, objects, routines, subroutines, firmware, and/or embedded code, for example.

Various examples of the disclosure have been described. Any combination of the described systems, operations, or functions is contemplated. These and other examples are within the scope of the following claims.

What is claimed is:

1. An oximetry device, comprising:

processing circuitry; and a memory comprising instructions that, when executed by the processing circuitry, cause the processing circuitry to:

determine, for a first light-emitting diode (LED) of a sensor, a first voltage at the first LED for a first current;

determine a second voltage at the first LED for a second current;

determine a first voltage difference value based on a respective difference between the first voltage and the second voltage;

receive calibration information from the sensor;

determine, for a second LED of the sensor, a third voltage at the second LED for the first current;

determine a fourth voltage at the second LED for the second current;

determine a second voltage difference value based on a respective difference between the third voltage and the fourth voltage;

determine a first temperature of the first LED based on the first voltage difference value and the calibration information;

determine a second temperature of the second LED based on the second voltage difference value and the calibration information;

determine a temperature difference between the first temperature and the second temperature;

compare the temperature difference to a threshold value; and validate the sensor as compatible with the oximetry device in response to the temperature difference being below the threshold value.

2. The oximetry device of claim 1, wherein the instructions, when executed by the processing circuitry, cause the processing circuitry to:

determine a low confidence metric for the sensor in response to the temperature difference being above the threshold value.

3. The oximetry device of claim 1, wherein the threshold value is stored in the memory of the oximetry device, received from the sensor, or both.

4. The oximetry device of claim 1, wherein the second voltage comprises a modified second voltage based on applying a ratio of the first current and the second current to the second voltage.

5. The oximetry device of claim 1, wherein the calibration information comprises a first calibration temperature for the first LED, a first slope factor for the first LED, a first calibration difference in a voltage value for the first LED, or any combination thereof.

6. The oximetry device of claim 5, wherein the first slope factor is associated with a first model of LED, a first type of LED, or both, that comprises the first LED.

7. The oximetry device of claim 5, wherein the first slope factor relates a respective change in temperature to a respective change in a respective voltage difference measured during a calibration process.

8. A method for validating a sensor, comprising:

determining, via processing circuitry and for a first light-emitting diode (LED) of the sensor, a first voltage at the first LED for a first current;

determining, via the processing circuitry, a second voltage at the first LED for a second current;

determining, via the processing circuitry, a first voltage difference value based on a respective difference between the first voltage and the second voltage;

determining, via the processing circuitry, a first temperature of the first LED based on the first voltage difference value and calibration information of the sensor;

determining, via the processing circuitry and for a second LED of the sensor, a third voltage at the second LED for the first current;

determining, via the processing circuitry, a fourth voltage at the second LED for the second current;

determining, via the processing circuitry, a second voltage difference value based on a respective difference between the third voltage and the fourth voltage;

determining, via the processing circuitry, a second temperature of the second LED based on the second voltage difference value and the calibration information of the sensor;

validating, via the processing circuitry, the sensor as accurate in response to a temperature difference between the first temperature and the second temperature being below a threshold value.

9. The method of claim 8, comprising:

adjusting, via the processing circuitry, an oxygen saturation value based on the first temperature, the second temperature, or both.

10. The method of claim 8, comprising:

receiving, at the processing circuitry, the calibration information comprising a first calibration temperature for the first LED, a first slope factor for the first LED, a first calibration difference in a voltage value for the first LED, or any combination thereof from the sensor.

* * * * *